(12) United States Patent
Nomura et al.

(10) Patent No.: US 6,387,908 B1
(45) Date of Patent: May 14, 2002

(54) EPOXYSUCCINAMIDE DERIVATIVES

(75) Inventors: Yutaka Nomura, Noda; Toshihiro Takahashi, Misato; Yasushi Yoshino, Funabashi; Koichiro Nishioka, Kasukabe, all of (JP)

(73) Assignee: Nippon Chemiphar Co., Ltd., Tokyo (JP)

( * ) Notice: Subject to any disclaimer, the term of this patent is extended or adjusted under 35 U.S.C. 154(b) by 0 days.

(21) Appl. No.: 09/508,026

(22) PCT Filed: Sep. 4, 1998

(86) PCT No.: PCT/JP98/03983

§ 371 Date: May 5, 2000

§ 102(e) Date: May 5, 2000

(87) PCT Pub. No.: WO99/11640

PCT Pub. Date: Mar. 11, 1999

(30) Foreign Application Priority Data

Sep. 4, 1997 (JP) .............................................. 9-257538

(51) Int. Cl.[7] ..................... A61K 31/336; C07D 303/46
(52) U.S. Cl. .................... 514/254.1; 514/326; 514/336; 514/394; 514/414; 514/422; 514/444; 514/471; 514/475; 544/374; 546/207; 546/281.7; 248/304.7; 248/467; 248/517; 549/60; 549/472; 549/473; 549/548; 549/549
(58) Field of Search ................................ 514/326, 475, 514/254.1, 336, 394, 414, 422, 444, 471; 549/512, 60, 472, 473, 548, 549; 544/374; 546/207, 281.7; 548/304.7, 467, 517

(56) References Cited

FOREIGN PATENT DOCUMENTS

JP           139182       *  5/1992

OTHER PUBLICATIONS

Ichihara et al., J. Pharm. Sci, vol. 80 No. 3, 1991.*

* cited by examiner

Primary Examiner—Richard L. Raymond
(74) Attorney, Agent, or Firm—Reed Smith LLP

(57) ABSTRACT

Epoxysuccinamide derivatives of the formula (1):

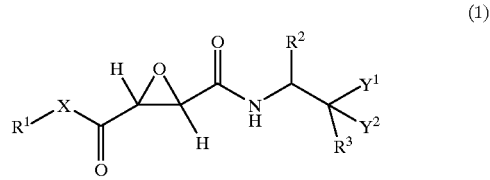

wherein $R^1$ is hydrogen, alkyl, alkenyl, alkynyl, aryl, or aralkyl; $R^2$ is alkyl, alkenyl, alkynyl, aryl, or aralkyl; $R^3$ is hydrogen, alkyl, alkenyl, alkynyl, aryl, aralkyl, heterocyclic, or heterocyclic-alkyl; X is —O— or —$NR^4$— ($R^4$ is hydrogen, alkyl, aryl, aralkyl, heterocyclic, or heterocyclic-alkyl); $Y^1$ is $OR^5$, $SR^6$, or $NR^7R^8$; and $Y^2$ is hydrogen or alkyl. The compounds are useful as remedies for bone diseases and arthritis.

15 Claims, No Drawings

EPOXYSUCCINAMIDE DERIVATIVES

This application is a 371 of PCT/JP98/03983, filed Sep. 4, 1998.

FIELD OF THE INVENTION

This invention relates to a novel epoxysuccinamide derivative and remedies for treating bone diseases and arthritis using the same.

BACKGROUND OF THE INVENTION

In the bone tissue, bone resorption and bone formation are continuously and simultaneously performed by osteoclasts and osteoblasts, respectively. The structure and amount of the bone is kept on their balance. However, if the excessive bone resorption continues for a long time, bone diseases such as osteoporosis develop In addition, malignant hypercalcemia and Paget's disease are accompanied by abnormal enhancement of excessive bone resorption.

The process of bone resorption by osteoclasts can be divided into two steps, namely, dissolution of minerals (i.e., decalcification) and degradation of bone matrix. The degradation of bone matricx is considered to occur by the action of lysosomal enzymes. According to recent studies, it is recognized that among the lysosomal enzymes, cathepsin L and its analogous enzyme, namely, cathepsin K, which are cysteine proteases, play a key role [Kakegawa and Katsunuma, Molecular Medicine, 30(10), 1310–1318 (1993), Tezuka et al., J. Biol. Chem., 269, 1106–1109(1994), Inui et al., J. Biol. Chem., 272, 8109(1997)]. Further, it has been reported that a cysteine protease inhibitor blocks the bone resorption [J. M. Delaisse et al., Biochem. Biophys., Res. Commun., 125, 441–447(1984)]. Therefore, compounds which inhibit action of cysteine protease such as cathepsin L are considered to be of value for treating bone diseases such as osteoporosis.

Japanese Patent Publication No. 61-55509 describes epoxysuccinic acid derivatives (i.e., epoxysuccinamic acid compounds) as compounds for inhibiting the action of a protease which have a thiol group participating in their action.

Further, it has been already proposed that certain epoxysuccinic acid derivatives be employed for treating bone diseases [Japanese Patent Provisional Publications No. 63-284127 and No. H2-218610].

Each of Japanese Patent Provisional Publications No. H8-41043 and H8-104684 describes that epoxysuccinamide derivatives having a specific chemical structure are effective for treating bone diseases.

WO 96/30354 describes the use of new epoxysuccinamides as remedies for treating bone diseases.

SUMMARY OF THE INVENTION

It is an object of the present invention to provide a compound and a pharmaceutical composition which are useful for prevention and treatment of bone diseases such as osteoporosis, malignant hypercalcemia and Paget's disease.

It is another object of the invention to provide a compound and a pharmaceutical composition which are useful for treating osteoarthritis and rheumatoid arthritis which are accompanied by abnormal enhancement of activities of cysteine proteases such as cathepsin B and cathepsin L.

It is a further object of the invention to provide a compound which is useful as a medicine for treating diseases in which cathepsin B and cathepsin L participate, such as muscular dystrophy and muscular atrophy.

The present inventors have earnestly studied to accomplish the above-mentioned objects and have found that new epoxysuccinamide derivatives having the below-mentioned formula (1) or their physiologically acceptable salts show a potent inhibitory action against cathepsin L and cathepsin L, and further show high effectiveness in inhibiting bone resorption and in treating a postmenopausal osteoporosis model, and furthermore show effectiveness in treating a rheumatoid arthritis model: salt:

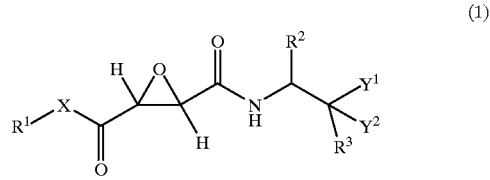

(1)

wherein
$R^1$ represents a hydrogen atom, an alkyl group having 1 to 10 carbon atoms, an alkenyl group having 2 to 10 carbon atoms, an alkynyl group having 2 to 10 carbon atoms, an aryl group having 6 to 20 carbon atoms, an aralkyl group comprising an aryl group having 6 to 20 carbon atoms and an alkyl group having 1 to 6 carbon atoms, a heterocyclic group having 3 to 12 carbon atoms, or a heterocyclic-alkyl group comprising a heterocyclic group having 3 to 12 carbon atoms and an alkyl group having 1 to 6 carbon atoms;

$R^2$ represents an alkyl group having 1 to 10 carbon atoms, an alkenyl group having 2 to 10 carbon atoms, an alkynyl group having 2 to 10 carbon atoms, an aryl group having 6 to 20 carbon atoms, an aralkyl group comprising an aryl group having 6 to 20 carbon atoms and an alkyl group having 1 to 6 carbon atoms, a heterocyclic group having 3 to 12 carbon atoms, or a heterocyclic-alkyl group comprising a heterocyclic group having 3 to 12 carbon atoms and an alkyl group having 1 to 6 carbon atoms;

$R^3$ represents a hydrogen atom, an alkyl group having 1 to 10 carbon atoms, an alkenyl group having 2 to 10 carbon atoms, an alkynyl group having 2 to 10 carbon atoms, an aryl group having 6 to 20 carbon atoms, an aralkyl group comprising an aryl group having 6 to 20 carbon atoms and an alkyl group having 1 to 6 carbon atoms, a heterocyclic group having 3 to 12 carbon atoms, or a heterocyclic-alkyl group comprising a heterocyclic group having 3 to 12 carbon atoms and an alkyl group having 1 to 6 carbon atoms;

X represents —O— or —NR$^4$— in which R$^4$ is a hydrogen atom, an alkyl group having 1 to 10 carbon atoms, an aryl group having 6 to 20 carbon atoms, an aralkyl group comprising an aryl group having 6 to 20 carbon atoms and an alkyl group having 1 to 6 carbon atoms, a heterocyclic group having 3 to 12 carbon atoms, or a heterocyclic-alkyl group comprising a heterocyclic group having 3 to 12 carbon atoms and an alkyl group having 1 to 6 carbon atoms;

$Y^1$ represents OR$^5$ in which R$^5$ is a hydrogen atom, an alkyl group having 1 to 10 carbon atoms, an aryl group having 6 to 20 carbon atoms, an aralkyl group comprising an aryl group having 6 to 20 carbon atoms and an alkyl group having 1 to 6 carbon atoms, an acyl group having 2 to 20 carbon atoms, a heterocyclic group having 3 to 12 carbon atoms, or a heterocyclic-alkyl group comprising a heterocyclic group having 3 to 12 carbon atoms and an alkyl group having 1 to 6 carbon atoms, SR$^6$ in which R$^6$ is a hydrogen atom, an alkyl group having 1 to 10 carbon atoms, an aryl group having 6 to 20 carbon atoms, an aralkyl group comprising an aryl group having 6 to 20 carbon atoms and an alkyl group having 1 to 6 carbon atoms, an acyl group having 2 to 20 carbon atoms, a heterocyclic group having 3 to 12 carbon atoms, or a heterocyclic-alkyl group comprising a heterocyclic group having 3 to 12 carbon atoms and an alkyl group having 1 to 6 carbon atoms, or $NR^7R^8$ in which $R^7$ is a hydrogen atom, an alkyl group having 1 to 10 carbon atoms, an aryl group having 6 to 20 carbon atoms, an aralkyl group comprising an aryl group having 6 to 20 carbon atoms and an alkyl group having 1 to 6 carbon atoms, an acyl group having 2 to 20 carbon atoms, a heterocyclic group having 3 to 12 carbon atoms, a heterocyclic-alkyl group comprising a heterocyclic group having 3 to 12 carbon atoms and an alkyl group having 1 to 6 carbon atoms, and $R^8$ is a hydrogen atom, an alkyl group having 1 to 10 carbon atoms, an aryl group having 6 to 20 carbon atoms, an aralkyl group comprising an aryl group having 6 to 20 carbon atoms and an alkyl group having 1 to 6 carbon atoms, a heterocyclic group having 3 to 12 carbon atoms, or a heterocyclic-alkyl group comprising a heterocyclic group having 3 to 12 carbon atoms and an alkyl group having 1 to 6 carbon atoms;

$Y^2$ represents a hydrogen atom or an alkyl group having 1 to 10 carbon atoms; or $Y^1$ and $Y^2$ in combination with each other can form =O, =S, =N—$R^9$ in which $R^9$ is a hydrogen atom, an alkyl group having 1 to 10 carbon atoms, an aryl group having 6 to 20 carbon atoms, an aralkyl group comprising an aryl group having 6 to 20 carbon atoms and an alkyl group having 1 to 6 carbon atoms, a heterocyclic group having 3 to 12 carbon atoms, or a heterocyclic-alkyl group comprising a heterocyclic group having 3 to 12 carbon atoms and an alkyl group having 1 to 6 carbon atoms, or =N—$OR^{10}$ in which $R^{10}$ is a hydrogen atom, an alkyl group having 1 to 10 carbon atoms, an aryl group having 6 to 20 carbon atoms, an aralkyl group comprising an aryl group having 6 to 20 carbon atoms and an alkyl group having 1 to 6 carbon atoms, a heterocyclic group having 3 to 12 carbon atoms, or a heterocyclic-alkyl group comprising a heterocyclic group having 3 to 12 carbon atoms and an alkyl group having 1 to 6 carbon atoms, provided that each of the alkyl groups for $R^5$ to $R^{10}$ can have one or more substituents selected from the group consisting of hydroxyl, amino, alkylamino having 1–6 carbon atoms, dialkylamino having 2–12 carbon atoms in total, alkoxy having 1–6 carbon atoms, carboxyl, alkoxycarbonyl having 2–7 carbon atoms, carbamoyl, alkylaminocarbonyl having 2–7 carbon atoms, dialkylaminocarbonyl having 3–13 carbon atoms in total, and guanidino; and each of the aryl groups and the heterocyclic groups for $R^1$ to $R^{10}$ may have one or more substituents selected from the group consisting of alkyl having 1–6 carbon atoms, hydroxyl, amino, alkylamino having 1–6 carbon atoms, dialkylamino having 2–12 carbon atoms in total, alkoxy having 1–6 carbon atoms, halogen, haloalkyl having 1–6 carbon atoms, cyano, nitro, carboxyl, alkoxycarbonyl having 2–7 carbon atoms, carbamoyl, alkylaminocarbonyl having 2–7 carbon atoms, dialkylaminocarbonyl having 3–13 carbon atoms in total, amidino, and guanidino.

Accordingly, the new epoxysuccinamide derivatives of, the above-mentioned formula (1) or their physiologically acceptable salts are effective for preventing or treating bone diseases and arthritis.

The preferred embodiments of the invention are described below.

1) $R^1$ of the formula (1) is a hydrogen atom or an alkyl group having 1 to 6 carbon atoms.

2) $R^2$ of the formula (1) is an alkyl group having 1 to 6 carbon atoms, phenyl, or benzyl.

3) $R^3$ of the formula (1) is a hydrogen atom or an aryl group having 6 to 20 carbon atoms.

4) X of the formula (1) is —O—.

5) $Y^1$ of the formula (1) is hydroxyl, an alkoxy group having 1 to 6 carbon atoms, acetoxy, or an aralkyloxy group comprising an aryl group having 6 to 20 carbon atoms and an alkyl group having 1 to 6 carbon atoms.

6) $R^2$ of the formula (1) is isobutyl or isopropyl, $R^3$ is a hydrogen atom, $Y^1$ is $OR^5$ whose $R^5$ has the meaning defined above, and $Y^2$ is a hydrogen atom 7) $R^2$ of the formula (1) is isobutyl or isopropyl, $R^3$ is an aryl group having 6 to 20 carbon atoms, $Y^1$ is $OR^5$ whose $R^5$ has the meaning defined above, and Y is a hydrogen atom.

8) $Y^1$ and $Y^2$ of the formula (1) in combination with each other form =O.

9) The physiologically acceptable salt is an alkali metal salt.

10) A pharmaceutical composition for treating bone diseases which comprises, as an active component, an epoxysuccinamide derivative of the formula (1) or its physiologically acceptable salt.

11) A pharmaceutical composition for treating arthritis which comprises, as an active component, an epoxysuccinamide derivative of the formula (1) or its physiologically acceptable salt.

PREFERRED EMBODIMENTS OF THE INVENTION

The epoxysuccinamide derivatives of the formula (1) according the present invention are further described below.

In the formula (1), $R^1$ is a hydrogen atom, an alkyl group having 1 to 10 carbon atoms (preferably an alkyl group having 1 to 6 carbon atoms, optionally a linear, branched, or cyclic alkyl group, e.g., methyl, ethyl, n-propyl, isopropyl, n-butyl, isobutyl, sec-butyl, tert-butyl, pentyl, isopentyl, hexyl, and cyclohexyl), an alkenyl group having 2 to 10 carbon atoms (preferably an alkenyl group having 2 to 6 carbon atoms, optionally a linear, branched, or cyclic alkenyl group, e.g., vinyl, 2-methyl-1-propenyl, and 2-cyclohexenyl), an alkynyl group having 2 to 10 carbon atoms (preferably an alkynyl group having 2 to 6 carbon atoms, optionally a linear or branched alkynyl group, e.g., 2-propynyl and 3-butynyl), an aryl group having 6 to 20 carbon atoms (e.g., phenyl and naphthyl), an aralkyl group comprising an aryl group having 6 to 20 carbon atoms and an alkyl group having 1 to 6 carbon atoms (e.g., benzyl, phenethyl and 3-phenylpropyl), a heterocyclic group having 3 to 12 carbon atoms (e.g., pyridyl, pyrrolidinyl, piperidinyl, furyl, and thienyl), or a heterocyclic-alkyl group comprising a heterocyclic group having 3 to 12 carbon atoms and an alkyl group having 1 to 6 carbon atoms (e.g., furfuryl, 2-thenyl, and 2-(3-pyridyl)ethyl).

$R^2$ is an alkyl group having 1 to 10 carbon atoms (preferably an alkyl group having 1 to 6 carbon atoms, optionally a linear, branched, or cyclic alkyl group, e.g, methyl, ethyl, n-propyl, isopropyl, n-butyl, isobutyl, sec-butyl, pentyl, isopentyl, hexyl, and cyclohexyl), an alkenyl group having 2 to 10 carbon atoms (preferably an alkenyl group having 2 to 6 carbon atoms, optionally a linear, a branched, or a cyclic alkenyl group, e.g., vinyl, 2-methyl-1-propenyl, and 2-cyclohexenyl), an alkynyl group having 2 to 10 carbon atoms (preferably an alkynyl group having 2 to 6 carbon atoms, optionally a linear or branched alkynyl group, e.g., 2-propynyl and 3-butynyl), an aryl group having 6 to 20 carbon atoms (e.g., phenyl and naphthyl), an aralkyl group comprising an aryl group having 6 to 20 carbon atoms and an alkyl group having 1 to 6 carbon atoms (e.g., benzyl, phenethyl and 3-phenylpropyl), a heterocyclic group having 3 to 12 carbon atoms (e.g., pyridyl, pyrrolidinyl, piperidinyl, furyl, and thienyl), or a heterocyclic-alkyl group comprising a heterocyclic group having 3 to 12 carbon atoms and an alkyl group having 1 to 6 carbon atoms (e.g., 3-indolylmethyl and 2-pyridylmethyl).

$R^3$ is a hydrogen atom, an alkyl group having 1 to 10 carbon atoms (preferably an alkyl group having 1 to 6 carbon atoms, optionally a linear, branched, or cyclic alkyl group, e.g., methyl, ethyl, n-propyl, isopropyl, n-butyl, isobutyl, sec-butyl, pentyl, isopentyl and hexyl), an alkenyl group having 2 to 10 carbon atoms (preferably an alkenyl group having 2 to 6 carbon atoms, optionally a linear, a branched, or a cyclic alkenyl group, e.g., vinyl, 2-methyl-1-propenyl, and 2-cyclohexenyl), an alkynyl group having 2 to 10 carbon atoms (preferably an alkynyl group having 2 to 6 carbon atoms, optionally a linear or branched alkynyl group, e.g., 2-propynyl and 3-butynyl), an aryl group having 6 to 20 carbon atoms (e.g., phenyl and naphthyl), an aralkyl group comprising an aryl group having 6 to 20 carbon atoms and an alkyl group having 1 to 6 carbon atoms (e.g., benzyl, phenethyl and 3-phenylpropyl), a heterocyclic group having 3 to 12 carbon atoms (e.g., pyridyl, pyrrolidinyl, piperidinyl, furyl, and thienyl), or a heterocyclic-alkyl group comprising a heterocyclic group having 3 to 12 carbon atoms and an alkyl group having 1 to 6 carbon atoms (e.g., 3-indolylmethyl and 2-pyridylmethyl).

X is —O— or —NR$^4$— (in which R$^4$ is a hydrogen atom, an alkyl group having 1 to 10 carbon atoms, an aryl group having 6 to 20 carbon atoms, an aralkyl group comprising an aryl group having 6 to 20 carbon atoms and an alkyl group having 1 to 6 carbon atoms, a heterocyclic group having 3 to 12 carbon atoms, or a heterocyclic-alkyl group comprising a heterocyclic group having 3 to 12 carbon atoms and an alkyl group having 1 to 6 carbon atoms). Preferred carbon atom numbers for these alkyl, aryl, aralkyl and heterocyclic-alkyl groups and their concrete examples are those described above for $R^1$, $R^2$ and $R^3$.

$Y^1$ is OR$^5$ (in which R$^5$ is a hydrogen atom, an alkyl group having 1 to 10 carbon atoms, an aryl group having 6 to 20 carbon atoms, an aralkyl group comprising an aryl group having 6 to 20 carbon atoms and an alkyl group having 1 to 6 carbon atoms, an acyl group having 2 to 20 carbon atoms, a heterocyclic group having 3 to 12 carbon atoms, or a heterocyclic-alkyl group comprising a heterocyclic group having 3 to 12 carbon atoms and an alkyl group having 1 to 6 carbon atoms), SR$^6$ (in which R$^6$ is a hydrogen atom, an alkyl group having 1 to 10 carbon atoms, an aryl group having 6 to 20 carbon atoms, an aralkyl group comprising an aryl group having 6 to 20 carbon atoms and an alkyl group having 1 to 6 carbon atoms, an acyl group having 2 to 20 carbon atoms, a heterocyclic group having 3 to 12 carbon atoms, or a heterocyclic-alkyl group comprising a heterocyclic group having 3 to 12 carbon atoms and an alkyl group having 1 to 6 carbon atoms), or NR$^7$R$^8$ (in which R$^7$ is a hydrogen atom, an alkyl group having 1 to 10 carbon atoms, an aryl group having 6 to 20 carbon atoms, an aralkyl group comprising an aryl group having 6 to 20 carbon atoms and an alkyl group having 1 to 6 carbon atoms, an acyl group having 2 to 20 carbon atoms, a heterocyclic group having 3 to 12 carbon atoms, a heterocyclic-alkyl group comprising a heterocyclic group having 3 to 12 carbon atoms and an alkyl group having 1 to 6 carbon atoms, and R$^8$ is a hydrogen atom, an alkyl group having 1 to 10 carbon atoms, an aryl group having 6 to 20 carbon atoms, an aralkyl group comprising an aryl group having 6 to 20 carbon atoms and an alkyl group having 1 to 6 carbon atoms, a heterocyclic group having 3 to 12 carbon atoms, or a heterocyclic-alkyl group comprising a heterocyclic group having 3 to 12 carbon atoms and an alkyl group having 1 to 6 carbon atoms). Preferred carbon atom numbers for these alkyl, aryl, aralkyl and heterocyclic-alkyl groups and their concrete examples are those described above for $R^1$, $R^2$ and $R^3$.

$Y^2$ is a hydrogen atom or an alkyl group having 1 to 10 carbon atoms (preferably an alkyl group having 1 to 6 carbon atoms, optionally a linear, branched, or cyclic alkyl group, e.g., methyl, ethyl, n-propyl, isopropyl, n-butyl, isobutyl, sec-butyl, pentyl, isopentyl and hexyl).

In the formula (1), $Y^1$ and $Y^2$ can form alternatively, in combination with each other, =O, =S, =N—R$^9$ (in which R$^9$ is a hydrogen atom, an alkyl group having 1 to 10 carbon atoms, an aryl group having 6 to 20 carbon atoms, an aralkyl group comprising an aryl group having 6 to 20 carbon atoms and an alkyl group having 1 to 6 carbon atoms, a heterocyclic group having 3 to 12 carbon atoms, or a heterocyclic-alkyl group comprising a heterocyclic group having 3 to 12 carbon atoms and an alkyl group having 1 to 6 carbon atoms), or =N—OR$^{10}$ (in which R$^{10}$ is a hydrogen atom, an alkyl group having 1 to 10 carbon atoms, an aryl group having 6 to 20 carbon atoms, an aralkyl group comprising an aryl group having 6 to 20 carbon atoms and an alkyl group having 1 to 6 carbon atoms, a heterocyclic group having 3 to 12 carbon atoms, or a heterocyclic-alkyl group comprising a heterocyclic group having 3 to 12 carbon atoms and an alkyl group having 1 to 6 carbon atoms). Preferred carbon atom numbers for these alkyl, aryl, aralkyl and heterocyclic-alkyl groups and their concrete examples are those described above for $R^1$, $R^2$ and $R^3$.

Particularly preferred epoxysuccinamide derivatives of the formula (1) and their physiologically acceptable salts are the following two cases.

1) an epoxysuccinamide derivative or its physiologically acceptable salt in which $R^2$ is isobutyl or isopropyl, $R^3$ is a hydrogen atom, $Y^1$ is OR$^5$ (R$^5$ has the meaning defined above), and $Y^2$ is a hydrogen atom Preferred carbon atom numbers for the alkyl, aryl, aralkyl and heterocyclic-alkyl groups in the groups of R$^5$ and their concrete examples are those described above for $R^1$, $R^2$, and $R^3$.

2) an epoxysuccinamide derivative or its physiologically acceptable salt in which $R^2$ is isobutyl or isopropyl, $R^3$ is an aryl group having 6 to 20 carbon atoms, $Y^1$ is OR$^5$ (R$^5$ has the meaning defined above), and $Y^2$ is a hydrogen atom. Preferred carbon atom numbers for the alkyl, aryl, aralkyl and heterocyclic-alkyl groups in the groups of R$^5$ and their concrete examples are those stated above for $R^1$, $R^2$, and $R^3$.

In the groups of $Y^1$ and $Y^2$ of the formula (1), each of the alkyl groups for R$^5$ to R$^{10}$ can have one or more substituents selected from the group consisting of hydroxyl, amino, alkylamino having 1–6 carbon atoms (e.g., methylamino, ethylamino, n-propylamino, and isobutylamino), dialkylamino having 2–12 carbon atoms in total (e.g., dimethylamino, methylethylamino and diethylamino), alkoxy having 1–6 carbon atoms (e.g., methoxy, ethoxy, n-propoxy, isopropoxy, and n-butoxy), carboxyl, alkoxycarbonyl having 2–7 carbon atoms (e.g., ethoxycarbonyl), carbamoyl, alkylaminocarbonyl having 2–7 carbon atoms (e.g, methylaminocarbonyl and ethylaminocarbonyl), dialkylaminocarbonyl having 3–13 carbon atoms in total (e.g., dimethylaminocarbonyl, diethylaminocarbonyl, methylethylaminocarbonyl and piperadinocarbonyl), and guanidino.

Each of the aryl groups and the heterocyclic groups for $R^1$ to R$^{10}$ may have one or more substituents selected from the group consisting of alkyl having 1–6 carbon atoms (e.g., methyl, ethyl, n-propyl, isopropyl, and n-butyl), hydroxyl, amino, alkylamino having 1–6 carbon atoms (e.g., methylamino, ethylamino, and n-propylamino), dialkylamino having 2–12 carbon atoms in total (e.g., dimethylamino, methylethylamino and diethylamino), alkoxy having 1–6 carbon atoms (e.g., methoxy, ethoxy, n-propoxy and isopropoxy), halogen (e.g., fluorine, chlorine, and bromine), haloalkyl having 1–6 carbon atoms (e.g., trifluoromethyl), cyano, nitro, carboxyl, alkoxycarbonyl having 2–7 carbon atoms (e.g., ethoxycarbonyl), carbamoyl, alkylaminocarbonyl having 2–7 carbon atoms (e.g., methylaminocarbonyl and ethylaminocarbonyl), dialkylaminocarbonyl having 3–13 carbon atoms in total (e.g., dimethylaminocarbonyl and methylethylaminocarbonyl), amidino, and quanidino.

The two carbon atoms of the oxirane ring of the aforementioned formula (1) both are asymmetric carbon atoms. The formula (1) means that the two carbonyl groups attached to the oxirane ring are in the trans conformation. Therefore, the epoxysuccinamide derivative of the invention can be either an optical isomer in the form of (T1) or (T2) mentioned below, or a mixture thereof.

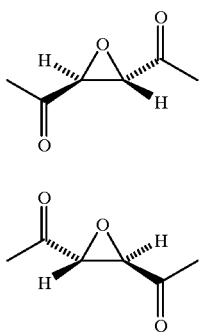

(T1)

(T2)

Examples of the epoxysuccinamide derivatives of the invention are set forth in the following Table 1 (Tables 1-1, 1-2, 1-3, and 1-4), wherein $R^1$, $R^2$, $R^3$, X, $Y^1$ and $Y^2$ mean those shown in the aforementioned formula (1). In the following Table 1, each symbol means the following H: hydrogen, Me: methyl, Et: ethyl, Ph: phenyl, Bn: benzyl, iPr: isopropyl, iBu: isobutyl, sBu: sec-butyl, tBu: tert-butyl, cHex: cyclohexyl, 4-MePh: 4-methylphenyl, 4-ClPh: 4-chlorophenyl, 4-tBuPh: 4-tert-butylphenyl, 4'-HOBn: 4'-hydroxybenzyl.

TABLE 1

| No. | $R^1$ | $R^2$ | $R^3$ | X | $Y^1$ | $Y^2$ |
|---|---|---|---|---|---|---|
| 1 | Et | iBu | Ph | O | OH | H |
| 2 | H | iBu | Ph | O | OH | H |
| 3 | iPr | iBu | Ph | O | OH | H |
| 4 | Et | iBu | Ph | NH | OH | H |
| 5 | Ph | iBu | Ph | NMe | OH | H |
| 6 | Et | iBu | 4-MePh | O | OH | H |
| 7 | Et | iBu | 4-ClPh | O | OH | H |
| 8 | Et | iBu | iPr | O | OH | H |
| 9 | Et | sBu | Ph | O | OH | H |
| 10 | Et | Ph | Ph | O | OH | H |
| 11 | Et | iBu | Ph | O | OMe | H |
| 12 | Et | iBu | Ph | O | OEt | H |
| 13 | Et | iBu | H | O | OH | H |
| 14 | Et | iBu | Me | O | OH | H |

TABLE 1-continued

| No. | $R^1$ | $R^2$ | $R^3$ | X | $Y^1$ | $Y^2$ |
|---|---|---|---|---|---|---|
| 15 | Et | iBu | Ph | O | =O (together with $Y^2$) | |
| 16 | Et | iPr | Ph | O | =O (together with $Y^2$) | |
| 17 | Et | iPr | Ph | O | =S (together with $Y^2$) | |
| 18 | H | sBu | Ph | O | OH | H |
| 19 | H | Ph | Ph | O | OH | H |
| 20 | H | iBu | Ph | O | OMe | H |
| 21 | H | iBu | H | O | OH | H |
| 22 | Et | iBu | Ph | O | acetoxy | H |
| 23 | Et | iBu | Ph | O | benzoyloxy | H |
| 24 | iPr | iBu | Ph | O | OMe | H |
| 25 | Bn | iBu | Ph | O | OMe | H |
| 26 | Et | iBu | Ph | O | benzyloxy | H |
| 27 | Et | iBu | H | O | benzyloxy | H |
| 28 | Et | iBu | H | O | 4'-chlorobenzyloxy | H |
| 29 | Et | iBu | H | O | 2'-methylbenzyloxy | H |
| 30 | Et | iBu | H | O | 3',4',5'-trimethoxybenzyloxy | H |
| 31 | Et | iPr | H | O | 2'-chlorobenzyloxy | H |
| 32 | Et | iPr | H | O | 4'-methylbenzyloxy | H |
| 33 | Et | iBu | H | O | 4'-amidinobenzyloxy | H |
| 34 | Et | iBu | H | O | 4'-guadinino-benzyloxy | H |
| 35 | Et | iBu | H | O | carboxymethoxy | H |
| 36 | Et | iBu | H | O | (2-ethoxycarbonylethyl)oxy | H |
| 37 | Et | iBu | H | O | (1-piperadinylcarbonyl)methoxy | H |
| 38 | Et | iBu | H | O | isobutylamino | H |
| 39 | Et | iBu | H | O | diethylamino | H |
| 40 | Et | iBu | H | O | benzylamino | H |
| 41 | Et | iBu | H | O | benzoylamino | H |
| 42 | Et | iBu | H | O | benzylcarbonylamino | H |
| 43 | Et | iBu | H | O | isobutoxy | H |
| 44 | Et | Bn | H | O | benzyloxy | H |
| 45 | Et | Bn | H | O | isobutoxy | H |
| 46 | Et | 4'-HOBn | H | O | benzyloxy | H |
| 47 | Et | iBu | H | O | diphenylmethoxy | H |
| 48 | H | iBu | Ph | O | benzyloxy | H |
| 49 | H | Bn | H | O | benzyloxy | H |
| 50 | H | iBu | H | O | benzyloxy | H |
| 51 | H | iBu | H | O | (4-guanidinobutyl)oxy | H |
| 52 | H | iBu | H | O | (2-ethylaminoethyl)oxy | H |
| 53 | H | iBu | H | O | (2-diethylaminoethyl)oxy | H |
| 54 | Et | iBu | cHex | O | OH | H |
| 55 | Et | iBu | cHex | O | OMe | H |
| 56 | Et | iBu | H | O | 2'-methylbenzyloxy | H |
| 57 | Et | iBu | H | O | 2',6'-dimethylbenzyloxy | H |
| 58 | Et | iBu | H | O | 4'-isopropylbenzyloxy | H |
| 59 | Et | iBu | H | O | 2'-chlorobenzyloxy | H |
| 60 | Et | iBu | H | O | 4'-trifluoromethylbenzyloxy | H |
| 61 | Et | iBu | H | O | 4'-cyanobenzyloxy | H |
| 62 | Et | iBu | H | O | 3'-aminobenzyloxy | H |
| 63 | Et | iBu | H | O | (3-pyridyl)methoxy | H |
| 64 | Et | iBu | H | O | (3-thienyl)methoxy | H |
| 65 | Et | iBu | H | O | (2-benzoimidazolyl)methoxy | H |
| 66 | Et | iBu | H | O | (1-naphthyl)methoxy | H |
| 67 | Et | iBu | H | O | 2-naphthyloxy | H |
| 68 | Et | iBu | H | O | phenoxy | H |
| 69 | Et | iBu | H | O | 2-phenylethoxy | H |
| 70 | Et | iBu | H | O | 3-phenylpropoxy | H |
| 71 | Et | iBu | H | O | ethoxy | H |
| 72 | Et | iBu | H | O | (3-methylbutyl)oxy | H |
| 73 | Et | iBu | H | O | hexyloxy | H |
| 74 | Et | iBu | H | O | cyclopropylmethoxy | H |
| 75 | Et | iBu | H | O | cyclohexylmethoxy | H |
| 76 | Et | iBu | H | O | (2-methyl-2-propenyl)oxy | H |
| 77 | Et | iBu | H | O | (3-methyl-2-butenyl)oxy | H |
| 78 | Et | iBu | H | O | 2-methoxyethoxy | H |

TABLE 1-continued

| No. | R¹ | R² | R³ | X | Y¹ | Y² |
|---|---|---|---|---|---|---|
| 79 | Et | iBu | H | O | (dimethylcarbamoyl)methoxy | H |
| 80 | Et | iBu | H | O | 3-(4-benzyl-1-piperadinyl)propoxy | H |
| 81 | Et | iBu | H | O | 4-diethylaminobutyloxy | H |
| 82 | iPr | iBu | H | O | isobutoxy | H |
| 83 | tBu | iBu | H | O | isobutoxy | H |
| 84 | cHex | iBu | H | O | isobutoxy | H |
| 85 | Ph | iBu | H | O | isobutoxy | H |
| 86 | 4-tBuPh | iBu | H | O | isobutoxy | H |
| 87 | H | iBu | H | O | isobutoxy | H |
| 88 | Et | iPr | H | O | isobutoxy | H |
| 89 | Et | sBu | H | O | isobutoxy | H |
| 90 | Et | iPr | H | O | benzyloxy | H |
| 91 | Et | Bn | H | O | benzyloxy | H |
| 92 | Et | iBu | H | O | 2-methyl-propionylamino | H |
| 93 | Et | iBu | H | O | hexanoylamino | H |
| 94 | Et | iBu | H | O | N-benzyl-N-methylamino | H |
| 95 | Et | iBu | H | O | N-hexyl-N-methylamino | H |

The epoxysuccinamide derivative of the invention can be employed in the form of a physiologically acceptable salt. For example, in the case that $R^1$ is a hydrogen atom and X is —O—, it forms a salt with an alkali metal (e.g., sodium or potassium), an alkaline earth metal (e.g., calcium), or an organic amine (e.g., triethylamine or pyridine).

Processes for preparing epoxysuccinamide derivatives of the invention are described below.

The epoxysuccinamide derivative of the invention can be prepared from the known compound by a process involving production of amide-bonding, esterification, or hydrolysis.

The respective reaction schemes are illustrated below.

1) Production of amide-bonding

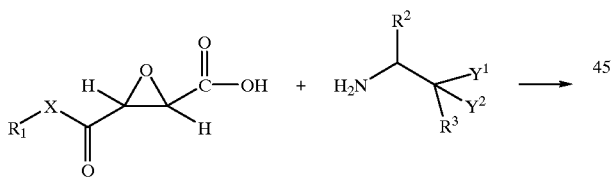

(1)

2) Production of amide-bonding (case of X=—NR⁴—)

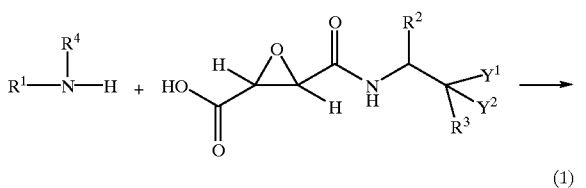

(1)

3) Esterification (case of $R^5$ is alkylcarbonyl, arylcarbonyl, aralkylcarbonyl, heterocyclic-carbonyl, or heterocyclic-alkylcarbonyl)

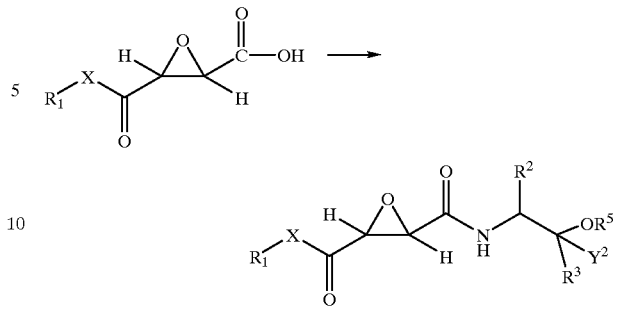

4) Esterification (case of X=—O— and $R^1 \neq$ hydrogen)

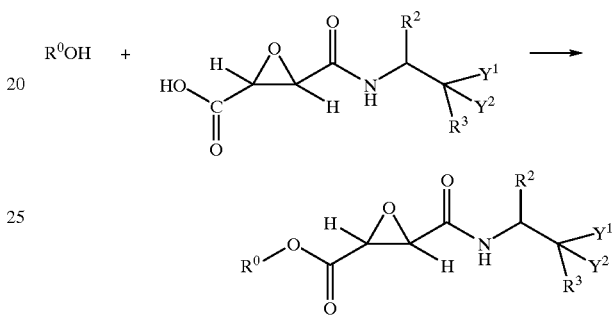

(in the above-illustrated reaction scheme, $R^0$ is the same as $R^1$ except that hydrogen is not included)

5) Hydrolysis (case of X=—O— and $R^1$=hydrogen)

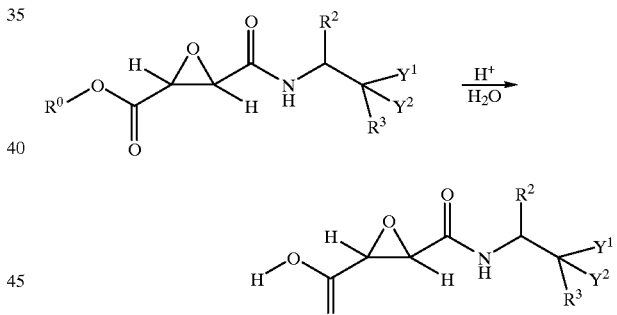

(in the above-illustrated reaction scheme, $R^0$ is the same as $R^1$ except that hydrogen is not included)

In performing the above-illustrated reactions, groups such as $R^1$ and/or $Y^1$ can be protected by a known protective group, if necessary.

In the preparation of an Epoxysuccinamide derivative of the invention, processes for preparing epoxysuccinamide derivatives described in Japanese Patent Publication No. 61-55509, Japanese Patent Provisional Publication No. 52-31024, H8-41043, H8-104684 and WO 96/30354 can be utilized. As for the detailed reaction conditions for preparing epoxysuccinamide derivatives of the invention, representative reaction conditions are stated in a great number of the working examples.

The epoxysuccinamide derivative of the invention can be administered by either oral or parenteral route. The oral formulation can be prepared in the form of tablets, capsules, powder, granules, or syrup. The parenteral administration can be performed through mucosal membrane, body surface, blood vessel, or tissue. The mucosal administration can be performed using ophthalmic solutions, inhalant, spray, or suppository. The surface administration can be performed using ointment. The administration through blood vessel and tissue can be performed using injections.

The oral formulation can be prepared using conventional excipient, disintegrator, binder, lubricant, dye and diluent. The excipient generally is glucose or lactose. The disintegrator can be starch or carboxymethyl cellulose calcium. The lubricant can be magnesium stearate or talc. The hinder can be hydroxypropyl cellulose, gelatin, or polyvinyl alcohol.

The pharmaceutical composition for parenteral administration can be prepared in the conventional way. For instance, the injection can be prepared using an ordinary distilled water for injection, saline, or Ringer's solution.

The dosage of the epoxysuccinamide derivative of the invention is in the range of 0.01 mg to 100 mg/day for adult in the case of using injection. In the case of oral administration, the dosage is in the range of 0.1 to 1 g/day for adult. The dosage can be increased or decreased depending on age, race, and conditions of patients.

Industrial Utility

The epoxysuccinamide derivative of the invention is a compound having inhibitory activities against cysteine proteases. The cysteine proteases encompass cathepsin L, cathepsin B, cathepsin K, calpain, etc. Therefore, an epoxysuccinamide derivative of the invention and its physiologically acceptable salt are expected to show pharmacological effects on diseases in which these proteases participate.

In more detail, examples of diseases in which cathepsin L and cathepsin K participate include bone diseases such as osteoporosis, malignant hypercalcemia, and Paget's disease. Therefore, the epoxysuccinamide derivative of the invention and its physiologically acceptable salt are useful as pharmaceuticals for preventing or treating these bone diseases.

It is reported that cathepsin L and cathepsin B participate in joint destruction in arthritis and that an inhibitor against these cathepsins are effective in suppressing the joint destruction in a rat arthritis model (Arthritis Rheum., 37, 236 (1994)). Further, it is reported that a cathepsin K inhibitor shows a similar effect in the rat arthritis model (J. Bone Miner. Res., 11, 246 (1996).

Therefore, the epoxysuccinamide derivative of the invention and its physiologically acceptable salt are useful in treating osteoarthritis and rheumatoid arthritis.

The epoxysuccinamide derivative of the invention is also effective as a cathepsin B inhibitor.

In more detail, examples of diseases in which a cysteine protease such as cathepsin B participates include muscular dystrophy and muscular atrophy (in which cathepsin B and calpain participate), Alzheimer's disease (in which calpain participates), and diseases which are considered to be caused by demyelination of neurocyte, such as multiple sclerosis and neuropathy of peripheral nervous system (in which calpain participates), cataract (in which calpain participates), allergic disorder (in which thiol protease participates), fulminant hepatitis (in which calpain participates), breast cancer, prostatic cancer, and prostatomegaly (in which calpain participates), hyperplasia and metastasis of cancer (in which cathepsin B and calpain participate), aggregation of platelet (in which calpain participates) (see Japanese Patent Provisional Publication No. H6-239835). Therefore, the epoxysuccinamide derivative of the invention is useful for treating and preventing these diseases.

The epoxysuccinamide derivative of the invention and its physiologically acceptable salt are expected to be useful for preventing and treating the above-mentioned diseases. Particularly, it is useful for prevention and treatment of bone diseases such as osteoporosis, malignant hypercalcemia and Paget's disease, and of arthritis such as osteoarthritis and rheumatoid arthritis.

The preparatory examples and results of pharmacological experiments of epoxysuccinamide derivatives (or their salts) of the invention are described below. In the examples, the compound No corresponds to "No." set forth in Table 1, except for the notation of absolute configuration.

EXAMPLE 1a

Ethyl (2S,3S)-3-[[1-(S)-[α-(R)-hydroxybenzyl]-3-methylbutyl]carbamoyl]oxirane-2-carboxylate
(Compound No. 1)

To a solution of (2S,3S)-3-ethoxycarbonyloxirane-2-carboxylic acid (696 mg, 4.78 mmol.) in ethyl acetate (15 mL) was added N-hydroxysuccinimide (550 mg, 4.78 mmol.) and then added N,N'-dicyclohexylcarbodiimide (986 mg, 4.78 mmol.) under chilling with ice. The resulting mixture was stirred at 5° C. for one hour, and to the mixture was added (1R,2S)-2-amino-4-methyl-1-phenyl-1-pentanol (1.01 g, 5.23 mmol.). The mixture was stirred overnight at room temperature for one hour. The resulting insoluble material was removed by filtration, and the filtrate was washed successively with 2N hydrochloric acid, water, an aqueous saturated sodium hydrogen carbonate solution, and an aqueous saturated sodium chloride solution, and then dried over anhydrous sodium sulfate. The solvent was distilled off under reduced pressure, and the residue was purified by middle pressure silica gel column chromatography (n-hexane/ethyl acetate=1/1), to give the desired compound as a white crystalline product (1.29 g, yield: 89%).

m.p.: 117.5–118.5° C.; $^1$H-NMR (CDCl$_3$) δ: 0.77 (3H, d, J=6 Hz), 0.83 (3H, d, J=7 Hz), 1.1–1.5 (3H, m), 1.31 (3H, t, J=7 Hz), 3.24 (1H, brs.), 3.37 (1H, d, J=2 Hz), 3.68 (1H, d, J=2 Hz), 4.2–4.3 (3H, m), 4.85 (1H, br.), 6.19 (1H, brd., J=9 Hz), 7.2–7.4 (5H, m). IR (KBr) cm$^{-1}$: 3540, 3280, 2960, 1750, 1665, 1565, 1550, 1280, 1270, 1205, 1025, 705.

EXAMPLE 1b

Ethyl (2R,3R)-3-[[1-(S)-[α-(R)-hydroxybenzyl]-3-methylbutyl]carbamoyl]oxirane-2-carboxylate
(Compound No. 1)

The titled compound was prepared in a manner similar to that of Example 1a.

$^1$H-NMR (CDCl$_3$) δ: 0.86 (3H, d, J=6 Hz), 0.89 (3H, d, J=7 Hz), 1.2–1.4 (2H, m), 1.32 (3H, t, J=7 Hz), 1.54 (1H, m), 2.87 (1H, d, J=4 Hz), 3.26 (1H, d, J=2 Hz), 3.66 (1H, d, J=2 Hz), 4.2–4.4 (2H, m), 4.76 (1H, t, J=4 Hz), 5.87 (1H, brd., J=9 Hz), 7.2–7.4 (5H, m).

EXAMPLE 2

(2S,3S)-3-[[1-(S)-[α-(R)-hydroxybenzyl]-3-methylbutyl]carbamoyl]oxirane-2-carboxylic acid
(Compound No. 2)

To a solution of ethyl (2S,3S)-3-[[1-(S)-[α-(R)-hydroxybenzyl]-3-methylbutyl]carbamoyl]oxirane-2-carboxylate (558 mg, 1.66 mmol.) in ethanol (4 mL) was dropwise added 0.5N potassium hydroxide/ethanol solution (4.0 mL, 2.0 mmol.) under chilling with ice. The mixture was stirred for 4 hours at room temperature, and made acidic to reach pH 1–2 by addition of water (40 mL) and 2N hydrochloric acid (approx. 2 mL). The acidic mixture was extracted with three portions of ethyl acetate. The three extracts were combined and washed successively with water and an aqueous saturated sodium chloride solution, and then dried over anhydrous sodium sulfate. The solvent was distilled off under reduced pressure to give the titled compound as a white amorphous product (490 mg, yield 96%).

$^1$H-NMR (CDCl$_3$/CD$_3$OD=1/1) δ: 0.77 (3H, d, J=6 Hz), 0.86 (3H, d, J=6 Hz), 1.2–1.6 (3H, m), 3.38 (1H, d, J=1 Hz), 3.58 (1H, d, J=1 Hz), 4.22 (1H, m), 4.75 (1H, d, J=4 Hz), 7.2–7.5 (5H, m).

EXAMPLE 3

Ethyl (2S,3S)-3-[[1-(S)-[α-(R)-hydroxybenzyl]-2-methylbutyl]carbamoyl]oxirane-2-carboxylate (Compound No. 9)

The procedures of Example 1a were repeated employing (2S,3S)-3-ethoxycarbonyloxirane-2-carboxlic acid and (1R, 2S)-2-amino-3-methyl-1-phenyl-1-pentanol (its preparation is described in the after-mentioned Reference Example 1), to prepare the titled compound.

$^1$H-NMR (CDCl$_3$) δ: 0.85 (3H, t, J=7 Hz), 0.9–1.0 (1H, m), 0.99 (3H, d, J=6 Hz), 1.31 (3H, t, J=7 Hz), 1.4–1.6 (2H, m), 2.61 (1H, d, J=4 Hz), 3.35 (1H, d, J=2 Hz), 3.64 (1H, d, J=2 Hz), 4.16 (1H, ddd, J=10,7,5 Hz), 4.19–4.32 (2H, m), 4.93 (1H, dd, J=5,4 Hz), 5.90 (1H, brd., J=10 Hz), 7.28–7.40 (5H, m).

EXAMPLE 4

Ethyl (2S,3S)-3-[[(αS,βR)-β-hydroxy-α-phenyl]phenethyl]carbamoyl]oxirane-2-carboxylate (Compound No. 10)

The procedures similar to those of Example 1a were repeated to prepare the titled compound m.p.: 170–171° C.; $^1$H-NMR (CDCl$_3$) δ: 1.29 (3H, t, J=7 Hz), 2.41 (1H, d, J=4 Hz), 3.39 (1H, d, J=2 Hz), 3.70 (1H, d, J2 Hz), 4.18–4.30 (2H, m), 5.09 (1H, t, J4 Hz), 5.23 (1H, dd, J=9, 4 Hz), 6.90 (1H, brd., J=9 Hz), 6.95–7.06 (5H, m), 7.19–7.28 (5H, m).

EXAMPLE 5

Ethyl (2S,3S)-3-[[1-(S)-[α-(R)-methoxybenzyl]-3-methylbutyl]carbamoyl]oxirane-2-carboxylate (Compound No. 11)

The procedures of Example 1a were repeated employing (2S,3S)-3-ethoxycarbonyloxirane-2-carboxylic acid and 1-(S)-[α-(R)-methoxybenzyl]-3-methylbutylamine (its preparation is described in the after-mentioned Reference Example 2) to prepare the titled compound.

m.p.: 108–109° C.; $^1$H-NMR (CDCl$_3$) δ: 0.73 (3H, d, J=6 Hz), 0.82 (3H, d, J=7 Hz), 1.15 (1H, m), 1.32 (3H, t, J=7 Hz), 1.28–1.40 (2H, m), 3.31 (3H, s), 3.34 (1H, d, J=2 Hz), 3.69 (1H, d, J=2 Hz), 4.16–4.34 (4H, m), 6.12 (1H, brd., J=10 Hz), 7.26–7.41 (5H, m). FAB-MS m/z 350 (MH$^+$).

EXAMPLE 6

Ethyl (2S,3S)-3-[[1-(S)-hydroxymethyl-3-methylbutyl]carbamoyl]oxirane-2-carboxylate (Compound No. 13)

The procedures similar to those of Example 1a were repeated to prepare the titled compound.

$^1$H-NMR (CDCl$_3$) δ: 0.92 (3H, d, J=6 Hz), 0.94 (3H, d, J=6 Hz), 1.32 (3H, t, J=7 Hz), 1.3–1.4 (2H, m), 1.5–1.6 (1H, m), 2.09 (1H, dd, J=2,6 Hz), 3.44 (1H, d, J=2 Hz), 3.58 (1H, m), 3.69 (1H, m), 3.70 (1H, d, J=2 Hz), 4.0–4.1 (1H, m), 4.2–4.3 (2H, m), 6.09 (1H, brd., J=7 Hz).

EXAMPLE 7

Ethyl (2S,3S)-3-[[1-(S)-benzoyl-3-methylbutyl]carbamoyl]oxirane-2-carboxylate (Compound No. 15)

The procedures similar to those of Example 1a were repeated to prepare the titled compound.

m.p.: 118–119° C.; $^1$H-NMR (CDCl$_3$) δ: 0.88 (3H, d, J=6 Hz), 1.06 (3H, d, J=6 Hz), 1.33 (3H, t, J=7 Hz), 1.4–1.7 (3H, m), 3.51 (1H, d, J=2 Hz), 3.71 (1H, d, J=2 Hz), 4.22–4.35 (2H, m), 5.66 (1H, m), 6.88 (1H, brd., J=8 Hz), 7.48–7.54 (2H, m), 7.62 (1H, m), 7.96–8.01 (2H, m).

EXAMPLE 8

Ethyl (2S,3S)-3-[[1-(S)-benzoyl-2-methylpropyl]carbamoyl]oxirane-2-carboxylate (Compound No. 16)

The procedures similar to those of Example 1a were repeated to prepare the titled compound.

$^1$H-NMR (CDCl$_3$) δ: 0.74 (3H, d, J=7 Hz), 1.00 (3H, d, J=7 Hz), 1.33 (3H, t, J=7 Hz), 2.22 (1H, m), 3.54 (1H, d, J=2 Hz), 3.73 (1H, d, J=2 Hz), 4.22–4.35 (2H, m), 5.56 (1H, dd, J=4,8 Hz), 6.95 (1H, brd., J=8 Hz), 7.48-7.54 (2H, m), 7.62 (1H, m), 7.95–8.01 (2H, m).

EXAMPLE 9

(2S,3S)-3-[[1-(S)-[α-(R)-hydroxybenzyl]-2-methylbutyl]carbamoyl]oxirane-2-carboxylic acid (Compound No. 18)

The procedures similar to those of Example 2 were repeated to prepare the titled compound.

$^1$H-NMR (CDCl$_3$) δ: 0.83 (3H, t, J=7 Hz), 0.9–1.0 (1H, m), 0.97 (3H, d, J=6 Hz), 1.40–1.55 (2H, m), 3.39 (1H, d, J=2 Hz), 3.71 (1H, d, J=2 Hz), 4.16 (1H, ddd, J=10,7,5 Hz), 4.9 (2H, br.), 4.96 (1H, d, J=5 Hz), 6.12 (1H, brd., J=10 Hz), 7.28–7.40 (5H, m).

EXAMPLE 10

(2S,3S)-3-[[(αS,βR)-β-hydroxy-α-phenyl]phenethyl]carbamoyl]oxirane-2-carboxylic acid (Compound No. 19)

The procedures similar to those of Example 2 were repeated to prepare the titled compound.

$^1$-NMR (CD$_3$OD/CDCl$_3$=1/1) δ: 3.37 (1H, d, J=2 Hz), 3.61 (1H, d, J=2 Hz), 5.03 (1H, d, J=5 Hz), 5.16 (1H, d, J=5 Hz), 7.1–7.3 (10H, m).

EXAMPLE 11

(2S,3S)-3-[[1-(S)-[α-(R)-methoxybenzyl]-3-methylbutyl]carbamoyl]oxirane-2-carboxylic acid (Compound No. 20)

The procedures similar to those of Example 2 were repeated to prepare the titled compound.

$^1$H-NMR (CD$_3$OD) δ: 0.79 (3H, d, J=6 Hz), 0.89 (3H, d, J=6 Hz), 1.42–1.58 (3H, m), 3.19 (1H, d, J=2 Hz), 3.25 (3H, s), 3.44 (1H, d, J=2 Hz), 4.07–4.15 (2H, m), 7.25–7.37 (5H, m).

EXAMPLE 12

(2S,3S)-3-[[1-(S)-hydroxymethyl-3-methylbutyl]carbamoyl]oxirane-2-carboxylic acid (Compound No. 21)

The procedures similar to those of Example 2 were repeated to prepare the titled compound
$^1$H-NMR (CD$_3$OD) δ: 0.92 (3H, d, J=7 Hz), 0.94 (3H, d, J=7 Hz), 1.3–1.5 (2H, m), 1.62 (1H, m), 3.4–3.5 (2H, m), 3.50 (1H, d, J=2 Hz), 3.58 (1H, d, J=2 Hz), 4.02 (1H, m). IR (KBr) cm$^{-1}$: 3342, 3267, 3099, 2958, 2872, 2598, 1736, 1666, 1560, 1468, 1387, 1367, 1240, 1070, 1030, 949, 895, 864, 785, 661.

EXAMPLE 13

Ethyl (2S,3S)-3-[[1-(S)-[α-(R)-acetoxybenzyl]-3-methylbutyl]carbamoyl]oxirane-2-carboxylate (Compound No 22)

In pyridine (0.6 mL) was dissolved ethyl (2S,3S)-3-[[1-(S)-[α-(R)-hydroxybenzyl]-3-methylbutyl]carbamoyl]oxirane- 2-carboxylate (300 mg, 0.894 mmol.). To the resulting solution was added acetic anhydride (0.085 mL, 0.901 mol.) under chilling with ice. The mixture was stirred for 18 hours at room temperature, and extracted with ether (8 mL, 3 portions) after addition of water (10 mL). The organic portion was washed successively with water, 1N hydrochloric acid, and an aqueous saturated sodium chloride solution, and dried over anhydrous sodium sulfate. The solvent was distilled off under reduced pressure. The residue was purified by silica gel column chromatography (n-hexane/ethyl acetate=2/1), to give the titled compound as a slightly brownish crystalline product (267 mg, yield: 79%).

m.p.: 94–96.5° C.; $^1$H-NMR (CDCl$_3$) δ: 0.83 (3H, d, J=7 Hz), 0.87 (3H, d, J=7 Hz), 1.19 (1H, m), 1.28 (1H, m), 1.31 (3H, t, J=7 Hz), 1.42 (1H, m), 2.13 (3H, s), 3.32 (1H, d, J=2 Hz), 3.70 (1H, d, J=2 Hz), 4.2–4.3 (2H, m), 4.45 (1H, m), 5.78 (1H, brd, J=10 Hz), 5.82 (1H, d, J=4 Hz), 7.2–7.4 (5H, m). IR (KBr) cm$^{-1}$: 3307, 2964, 2933, 2873, 1759, 1741, 1672, 1552, 1497, 1471, 1435, 1369, 1336, 1317, 1302, 1300, 1234, 1200, 1151, 1097, 1026, 966, 899, 870, 773, 739, 704, 619, 633, 598, 577, 486.

EXAMPLE 14

Isopropyl (2S,3S)-3-[[1-(S)-[α-(R)-methoxybenzyl]-3-methylbutyl]carbamoyl]oxirane-2-carboxylate (Compound No. 24)

To a solution of (2S,3S)-3-[[1-(S)-[α-(R)-methoxybenzyl]-3-methylbutyl]carbamoyl]oxirane-2-carboxylic acid (105 mg, 0.327 mmol), 2-propanol (30 μl, 0.40 mmol.) and 4-dimethylaminopyridine (8 mg, 0.07 mmol.) in anhydrous dichloromethane (4 mL) was added 1,3-dicyclohexylcarbodiimide (75 mg, 0.36 mmol.) under chilling with ice. The resulting mixture was stirred at 5° C. for 30 minutes, and then stirred overnight at room temperature. The mixture was placed under reduced pressure to distill off the solvent. The residue was mixed with ethyl acetate and 10% citric acid, and the insoluble material was removed by filtration. The filtrate was successively washed with water, aqueous saturated sodium hydrogen carbonate solution, and aqueous saturated sodium chloride solution, and dried over anhydrous sodium sulfate. The solvent was distilled off under reduced pressure. The residue was purified by middle pressure silica gel column chromatography (n-hexane/ethyl acetate=3/1), to give the titled compound as a white crystalline product (70 mg, yield: 59%).

$^1$H-NMR (CDCl$_3$) δ: 0.73 (3H, d, J=6 Hz), 0.82 (3H, d, J=6 Hz), 1.15 (1H, m), 1.29 (6H, d, J=6 Hz), 1.25–1.40 (2H, m), 3.30 (4H, brs.), 3.68 (1H, d, J=2 Hz), 4.20 (1H, m), 4.30 (1H, d, J=4 Hz), 5.11 (1H, m), 6.14 (1H, brd., J=10 Hz), 7.24–7.42 (5H, m).

EXAMPLE 15

Benzyl (2S,3S)-3-[[1-(S)-[α-(R)-methoxybenzyl]-3-methylbutyl]carbamoyl]oxirane-2-carboxylate (Compound No. 25)

The procedures similar to those of Example 14 were repeated to prepare the titled compound.
$^1$H-NMR (CDCl$_3$) δ: 0.71 (3H, d, J=6 Hz), 0.80 (3H, d, J=6 Hz), 1.14 (1H, m), 1.2–1.4 (2H, m), 3.30 (3H, s), 3.38 (1H, d, J=2 Hz), 3.71 (1H, d, J=2 Hz), 4.18 (1H, m), 4.29 (1H, d, J=4 Hz), 5.18 (1H, d, J=12 Hz), 5.26 (1H, d, J=12 Hz), 6.11 (1H, brd., J=10 Hz), 7.24–7.42 (5H, m).

EXAMPLE 16

Ethyl (2S,3S)-3-[[1-(S)-[α-(R)-benzyloxybenzyl]-3-methylbutyl]carbamoyl]oxirane-2-carboxylate (Compound No. 26)

The procedures similar to those of Example 1a were repeated to prepare the titled compound
$^1$H-NMR (CDCl$_3$) δ: 0.70 (3H, d, J=7 Hz), 0.80 (3H, d, J=7 Hz), 1.15 (1H, m), 1.2–1.4 (2H, m), 1.32 (3H, t, J=7 Hz), 3.34 (1H, d, J=2 Hz), 3.59 (1H, d, J=2 Hz), 4.1–4.3 (4H, m), 4.52 (1H, d, J=4 Hz), 4.61 (1H, d, J=12 Hz), 6.14 (1H, brd., J=9 Hz), 7.2–7.4 (10H, m).

EXAMPLE 17

Ethyl (2S,3S)-3-[[1-(S)-benzyloxymethyl-3-methylbutyl]carbamoyl]oxirane-2-carboxylate (Compound No. 27)

The procedures similar to those of Example 1a were repeated to prepare the titled compound.
$^1$H-NMR (CDCl$_3$) δ: 0.90 (3H, d, J=6 Hz), 1.32 (3H, t, J=7 Hz), 1.3–1.5 (3H, m), 3.42 (1H, d, J=2 Hz), 3.42–3.49 (2H, m), 3.66 (1H, d, J=2 Hz), 4.16 (1H, m), 4.2–4.3 (2H, m), 4.48, 4.53 (2H, each d, J=12 Hz), 6.17 (1H, brd., J=9 Hz), 7.2–7.4 (5H, m).

EXAMPLE 18a

Ethyl (2S,3S)-3-[[1-(S)-isobutoxymethyl-3-methylbutyl]carbamoyl]oxirane-2-carboxylate (Compound No. 43)

The procedures similar to those of Example 1a were repeated to prepare the titled compound.
$^1$H-NMR (CDCl$_3$) δ: 0.89 (6H, d, J=7Hz), 0.91 (6H, d, J=7 Hz), 1.31 (3H, t, J=7 Hz), 1.3–1.6 (3H, m), 1.85 (1H, m), 3.1–3.2 (2H, m), 3.40 (2H, d, J=4 Hz), 3.43 (1H, d, J=2 Hz), 3.67 (1H, d, J=2 Hz), 4.13 (1H, m), 4.2–4.3 (2H, m), 6.19 (1H, brd., J=9 Hz).

EXAMPLE 18b

Ethyl (2S,3S)-3-[[1-(R)-isobutoxymethyl-3-methylbutyl]carbamoyl]oxirane-2-carboxylate (Compound No. 43)

The procedures similar to those of Example 1a were repeated to prepare the titled compound.

m.p.: 60–63° C.; $^1$H-NMR (CDCl$_3$) δ: 0.89 (3H, d, J=7 Hz), 0.91 (6H, d, J=9 Hz), 0.93 (3H, d, J=6 Hz), 1.31 (3H, t, J=7 Hz), 1.3–1.7 (3H, m), 1.83 (1H, m), 3.1–3.2 (2H, m), 3.34 (1H, dd, J=4,9 Hz), 3.35 (1H, dd, J=4,9 Hz), 3.43 (1H, d, J=2 Hz), 3.66 (1H, d, J=2 Hz), 4.13 (1H, m) 4.2–4 3 (2H, m), 6.09 (1H, brd., J=9 Hz).

EXAMPLE 19

Ethyl (2S,3S)-3-[[1-(S)-benzyloxymethyl-2-phenylethyl]carbamoyl]oxirane-2-carboxylate (Compound No. 44)

The procedures similar to those of Example 1a were repeated to prepare the titled compound.

$^1$H-NMR (CDCl$_3$) δ: 1.30 (3H, t, J=7 Hz), 2.81 (1H, dd, J=7,14 Hz), 2.90 (1H, dd, J=7,14 Hz), 3.12 (1H, d, J=2 Hz), 3.59 (1H, d, J=2 Hz), 3.40–3.47 (2H, m), 4.2–4.4 (3H, m), 4.49, 4.54 (2H, each d, J=12 Hz), 6.28 (1H, brd, J=8 Hz), 7.1–7.4 (10H, m).

EXAMPLE 20

Ethyl (2S,3S)-3-[[1-(S)-isobutoxymethyl-2-phenylethyl]carbamoyl]oxirane-2-carboxylate (Compound No. 45)

The procedures similar to those of Example 1a were repeated to prepare the titled compound.

$^1$H-NMR (CDCl$_3$) δ: 0.93 (3H, d, J=7 Hz), 0.94 (3H, d, J=7 Hz), 1.30 (3H, t, J=7 Hz), 1.88 (1H, m), 2.81 (1H, dd, J=7,14 Hz), 2.90 (1H, dd, J=8,14 Hz), 3.15 (1H, d, J=2 Hz), 3.15–3.21 (2H, m), 3.35 (1H, dd, J=4,9 Hz), 3.38 (1H, dd, J=3,9 Hz), 3.61 (1H, d, J=2 Hz), 4.2–4.3 (3H, m), 6.29 (1H, brd., J=9 Hz), 7.1–7.3 (5H, m).

EXAMPLE 21

Ethyl (2S,3S)-3-[[1-(S)-diphenylmethoxymethyl-3-methylbutyl]carbamoyl]oxirane-2-carboxylate (Compound No. 47)

The procedures of Example 1a were repeated employing (2S,3S)-3-ethoxycarbonyloxirane-2-carboxylic acid and 1-(S)-(diphenylmethoxy)methyl-3-methylbutylamine (its preparation is described in the after-mentioned Reference Example 3), to prepare the titled compound $^1$H-NMR (CDCl$_3$) δ: 0.90 (6H, d, J=6 Hz), 1.32 (3H, t, J=7 Hz), 1.40–1.52 (3H, m), 3.43 (1H, d, J=2 Hz), 3.44 (1H, dd, J=9,3 Hz), 3.48 (1H, dd, J=9,4 Hz), 3.65 (1H, d, J=2 Hz), 4.16 (1H, m), 4.21–4.33 (2H, m), 5.32 (1H, s), 6.21 (1H, brd., J=9 Hz), 7.22–7.36 (10H, m).

EXAMPLE 22

(2S,3S)-3-[[1-(S)-[α-(R)-(benzyloxy)benzyl]-3-methylbutyl]carbamoyl]oxirane-2-carboxylic acid (Compound No. 48)

The procedures similar to those of Example 2 were repeated to prepare the titled compound.

$^1$H-NMR (CDCl$_3$) δ: 0.69 (3H, d, J=6 Hz), 0.80 (3H, d, J=6 Hz), 1.15 (1H, ddd, J=3,10,14 Hz), 1.31 (1H, m), 1.42 (1H, ddd, J=4,12,14 Hz), 3.38 (1H, d, J=2 Hz), 3.63 (1H, J=2 Hz), 4.17 (1H, m), 4.27 (1H, d, J=12 Hz), 4.52 (1H, d, J=3 Hz), 4.63 (1H, d, J=12 Hz), 6.25 (1H, brd., J=10 Hz), 7.3–7.4 (10H, m). IR (KBr) cm$^{-1}$: 3404, 3280, 3088, 3032, 2958, 2870, 2605, 1740, 1664, 1547, 1497, 1445, 1387, 1367, 1265, 1209, 1155, 1088, 1068, 1028, 987, 850, 750, 702, 656, 598, 492, 467.

EXAMPLE 23

Sodium (2S,3S)-3-[[1-(S)-benzyloxymethyl-2-phenylethyl]carbamoyl]oxirane-2-carboxylate (Compound No. 49)

In ethanol (4 mL) was dissolved ethyl (2S,3S)-3-[[1-(S)-benzyloxymethyl-2-phenylethyl]carbamoyl]oxirane-2-carboxylate (101 mg, 0.263 mmol.). To the solution was added 0.5N sodium hydroxide/ethanol solution (0.63 mL, 0.315 mmol.) under chilling with ice. The mixture was stirred for 4 hours at room temperature and placed under reduced pressure to distill off the solvent (in a bath maintained at a temperature of lower than 35° C.). The residue was dissolved in water (5 mL), and washed with ether (5 mL). The aqueous portion was made acidic to reach pH 1–2 by addition of 2N hydrochloric acid, and extracted with 3 portions of ethyl acetate (5 mL). The organic portion was washed with aqueous saturated sodium chloride solution and dried over anhydrous sodium sulfate. The solvent was distilled off under reduced pressure to leave a free base as colorless oil (91.9 mg, quantitative). The free base was dissolved in ethyl acetate (6 mL) and combined with an aqueous solution (6 mL) of sodium hydrogen carbonate (21.5 mg, 0.256 mmol.). The mixture was violently shaken in a separating funnel. The aqueous portion was taken out and placed under reduced pressure (in a bath maintained at a temperature of lower than 35° C.) to distill off the solvent, to give the titled compound as a white amorphous product (88.8 mg, yield: 92%).

$^1$H-NMR (D$_2$O) δ: 2.69 (1H, dd, J=9,14 Hz), 2.96 (1H, dd, J=5,14 Hz), 3.10 (1H, d, J=2 Hz), 3.38 (1H, d, J=2 Hz), 3.59 (1H, dd, J=7,11 Hz), 3.69 (1H, dd, J=4,11 Hz), 4.35 (1H, m), 4.57, 4.63 (2H, each d, J=12 Hz), 7.2–7.5 (10H, IR (KBr) cm$^{-1}$: 3415, 3265, 3030, 2864, 1655, 1620, 1554, 1497, 1454, 1385, 1275, 1207, 1190, 1124, 1090, 1028, 953, 899, 845, 779, 744, 698, 598, 507.

EXAMPLE 24

Sodium (2S,3S)-3-[[1-(S)-benzyloxymethyl-3-methylbutyl]carbamoyl]oxirane-2-carboxylate (Compound No 50)

The procedures similar to those of Example 23 were repeated to prepare the titled compound.

$^1$H-NMR (D$_2$O) δ: 0.86 (3H, d, J=6 Hz), 0.89 (3H, d, J=6 Hz), 1.3–1.4 (2H, m), 1.56 (1H, m), 3.40 (1H, s), 3.47 (1H, s), 3.50 (1H, dd, J=7,11 Hz), 3.58 (1H, dd, J=4,11 Hz), 4.16 (1H, m), 4.55, 4.61 (2H, each d, J=12 Hz), 7.4–7.5 (5H, m). IR (KBr) cm$^{-1}$: 3462, 3413, 3259, 3089, 3032, 2956, 2868, 1659, 1637, 1560, 1497, 1454, 1437, 1398, 1313, 1261, 1207, 1120, 1099, 1030, 895, 860, 739, 698, 621, 498.

EXAMPLE 25

Ethyl (2S,3S)-3-[[1-(S)-(benzoylamino)methyl-3-methylbutyl]carbamoyl]oxirane-2-carboxylate (Compound No. 41)

The procedures similar to those of Example 1a were repeated to prepare the titled compound.

m.p.: 125.5–129° C.; $^1$H-NMR (CDCl$_3$) δ: 0.93 (3H, d, J=7 Hz), 0.95 (3H, d, J=7 Hz), 1.30 (3H, t, J=7 Hz), 1.4–1.5 (2H, m), 1.5–1.6 (1H, m), 3.42 (1H, d, J=2 Hz), 3.66 (1H, d, J=2 Hz), 3.4–3.6 (2H, m), 4.1–4.2 (1H, m), 4.2–4.3 (2H, m), 6.23 (1H, brd., J=9 Hz), 6.92 (1H, br.), 7.4–7.5 (3H, m), 7.7–7.8 (2H, m). IR (KBr) cm$^{-1}$: 3413, 3286, 3101, 2956, 2875, 1755, 1664, 1635, 1560, 1491, 1439, 1371, 1348, 1325, 1294, 1277, 1246, 1230, 1205, 1132, 1028, 985, 899, 704, 696.

EXAMPLE 26

Ethyl (2S,3S)-3-[[1-(S)-[(R)-cyclohexyl(methoxy)methyl]-3-methylbutyl]carbamoyl]oxirane-2-carboxylate (Compound No. 55)

The procedures similar to those of Example 1a were repeated to prepare the titled compound.

$^1$H-NMR (CDCl$_3$) δ: 0.87 (3H, d, J=7 Hz), 0.91 (3H, d, J=7 Hz), 1.03 (1H, m), 1.1–1.3 (4H, m), 1.33 (3H, t, J=7 Hz), 1.3–1.5 (4H, m), 1.5–1.8 (4H, m), 1.97 (1H, m), 2.89 (1H, dd, J=3,9 Hz), 3.42 (1H, d, J=2 Hz), 3.67 (1H, d, J=2 Hz), 4.11 (1H, m), 4.2–4.3 (2H, m), 6.11 (1H, brd., J=10 Hz).

EXAMPLE 27

Ethyl (2S,3S)-3-[[1-(S)-(4-isopropylbenzyloxy)methyl-3-methylbutyl]carbamoyl]oxirane-2-carboxylate (Compound No. 58)

The procedures similar to those of Example 1a were repeated to prepare the titled compound.

$^1$H-NMR (CDCl$_3$) δ: 0.90 (6H, d, J=6 Hz), 1.25 (6H, d, J=7 Hz), 1.32 (3H, t, J=7 Hz), 1.3–1.6 (3H, m), 2.91 (1H, m), 3.41 (1H, d, J=2 Hz), 3.4–3.5 (2H, m), 3.65 (1H, d, J=2 Hz), 4.13 (1H, m), 4.2–4.3 (2H, m), 4.45 (1H, d, J=12 Hz), 4.49 (1H, d, J=12 Hz), 6.17 (1H, brd., J=9 Hz), 7.2–7.3 (4H, m).

EXAMPLE 28

Ethyl (2S,3S)-3-[[1-(S)-(2-chlorobenzyloxy)methyl-3-methylbutyl]carbamoyl]oxirane-2-carboxylate (Compound No. 59)

The procedures similar to those of Example 1a were repeated to prepare the titled compound.

$^1$H-NMR (CDCl$_3$): 0.91 (6H, d, J=6 Hz), 1.31 (3H, t, J=7 Hz), 1.3–1.6 (3H, m), 3.42 (1H, d, J=2 Hz), 3.52 (1H, dd, J=3,9 Hz), 3.55 (1H, dd, J=4,9 Hz), 3.66 (1H, d, J=2 Hz), 4.1–4.3 (3H, m), 4.58 (1H, d, J=13 Hz), 4.62 (1H, d, J=13 Hz), 6.20 (1H, brd., J=9 Hz), 7.2–7.5 (4H, m).

EXAMPLE 29

Ethyl (2S3S)-3-[[1-(S)-(3-aminobenzyloxy)methyl-3-methylbutyl]carbamoyl]oxirane-2-carboxylate (Compound No. 62)

The procedures similar to those of Example 1a were repeated to prepare the titled compound.

$^1$H-NMR (CDCl$_3$) δ: 0.90 (6H, d, J=6 Hz), 1.32 (3H, t, J=7 Hz), 1.3–1.6 (3H, m), 3.40–3.48 (3H, m), 3.66 (1H, d, J=2 Hz), 4.14 (1H, m), 4.20–4.33 (2H, m), 4.42 (2H, s), 6.19 (1H, brd., J=9 Hz), 6.58–6.70 (3H, m), 7.13 (1H, t, J=8 Hz).

EXAMPLE 30

Ethyl (2S,3S)-3-[[1-(S)-(3-pyridyl)methoxymethyl-3-methylbutyl]carbamoyl]oxirane-2-carboxylate (Compound No. 63)

The procedures similar to those of Example 1a were repeated to prepare the titled compound.

$^1$H-NMR (CDCl$_3$) δ: 0.90 (3H, d, J=7 Hz), 0.91 (3H, d, J=7 Hz), 1.32 (3H, t, J=7 Hz), 1.3–1.6 (3H, m), 3.42 (1H, d, J=2 Hz), 3.47 (1H, dd, J=9,4 Hz), 3.51 (1H, dd, J=9,4 Hz), 3.68 (1H, d, J=2 Hz), 4.17 (1H, m), 4.2–4.3 (2H, m), 4.50 (1H, d, J=12 Hz), 4.56 (1H, d, J=12 Hz), 6.12 (1H, brd., J=9 Hz), 7.30 (1H, dd, J=5,8 Hz), 7.65 (1H, dt, J=2,8 Hz), 8.56 (2H, dd, J=2,5 Hz).

EXAMPLE 31

Ethyl (2S,3S)-3-[[1-(S)-(3-thienyl)methoxymethyl-3-methylbutyl]carbamoyl]oxirane-2-carboxylate (Compound No. 64)

The procedures similar to those of Example 1a were repeated to prepare the titled compound.

m.p.: 61.0–62.5° C.; $^1$H-NMR (CDCl$_3$) δ: 0.90 (6H, d, J=6 Hz), 1.32 (3H, t, J=7 Hz), 1.3–1.6 (3H, m), 3.42 (1H, d, J=2 Hz), 3.43 (1H, dd, J=3,10 Hz), 3.46 (1H, dd, J=3,10 Hz), 3.66 (1H, d, J=2 Hz), 4.15 (1H, m), 4.2–4.3 (2H, m), 4.49 (1H, d, J=12 Hz), 4.54 (1H, d, J=12 Hz), 6.14 (1H, brd., J=9 Hz), 7.05 (1H, dd, J=1,5 Hz), 7.19 (1H, dd, J=1,3 Hz), 7.32 (1H, dd, J=3,5 Hz). IR (KBr) cm$^{-1}$: 3267, 3242, 3089, 2960, 2871, 1741, 1687, 1560, 1473, 1464, 1439, 1367, 1346, 1344, 1275, 1252, 1207, 1205, 1157, 1086, 1055, 1032, 962, 920, 895, 858, 833, 818, 796, 690, 688, 636, 596, 561.

EXAMPLE 32

Ethyl (2S,3S)-3-[[1-(S)-(2-benzimidazolyl)methoxymethyl-3-methylbutyl]carbamoyl]oxirane-2-carboxylate (Compound No. 65)

The procedures similar to those of Example 1a were repeated to prepare the titled compound.

$^1$H-NMR (CDCl$_3$) δ: 0.88 (3H, d, J=6 Hz), 0.89 (3H, d, J=6 Hz), 1.31 (3H, t, J=7 Hz), 1.24–1.40 (2H, m), 1.52 (1H, m), 3.46 (1H, d, J=2 Hz), 3.54 (1H, dd, J=7,10 Hz), 3.58 (1H, dd, J=4,10 Hz), 3.72 (1H, d, J=2 Hz), 4.20–4.31 (3H, m), 4.80 (1H, d, J=14 Hz), 4.84 (1H, d, J=14 Hz), 6.25 (1H, brd., J=9 Hz), 7.23–7.25 (2H, m), 7.60 (2H, brs.).

EXAMPLE 33

Ethyl (2S,3S)-3-[[1-(S)-phenoxymethyl-3-methylbutyl]carbamoyl]oxirane-2-carboxylate (Compound No. 68)

The procedures similar to those of Example 1a were repeated to prepare the titled compound.

$^1$H-NMR (CDCl$_3$) δ: 0.93 (3H, d, J=6 Hz), 0.95 (3H, d, J=6 Hz), 1.32 (3H, t, J=7 Hz), 1.46–1.62 (3H, m), 3.46 (1H, d, J=2 Hz), 3.68 (1H, d, J=2 Hz), 3.95 (1H, dd, J=3,9 Hz), 4.00 (1H, dd, J=4,9 Hz), 4.20–4.39 (3H, m), 6.23 (1H, brd., J=9 Hz), 6.89 (2H, brd., J=8 Hz), 6.97 (1H, brt. J=7 Hz), 7.25–7.32 (2H, m).

EXAMPLE 34

Ethyl (2S,3S)-3-[[1-(S)-(2-phenylethoxy)methyl-3-methylbutyl]carbamoyl]oxirane-2-carboxylate (Compound No. 69)

The procedures similar to those of Example 1a were repeated to prepare the titled compound.

$^1$H-NMR (CDCl$_3$) δ: 0.88 (3H, d, J=6 Hz), 0.89 (3H, d, J=6 Hz), 1.2–1.6 (3H, m), 1.32 (3H, t, J=7 Hz), 2.86 (2H, t, J=7 Hz), 3.37–3.45 (3H, m), 3.59–3.70 (3H, m), 4.09 (1H, m), 4.20–4.33 (2H, m), 6.08 (1H, brd., J=9 Hz), 7.16–7.32 (5H, m).

EXAMPLE 35

Ethyl (2S,3S)-3-[[1-(S)-(3-methylbutyloxy)methyl-3-methylbutyl]carbamoyl]oxirane-2-carboxylate (Compound No. 72)

The procedures similar to those of Example 1a were repeated to prepare the titled compound.

¹H-NMR (CDCl₃) δ: 0.90 (6H, d, J=6 Hz), 0.91 (6H, d, J=6 Hz), 1.32 (3H, t, J=7 Hz), 1.3–1.6 (5H, m), 1.68 (1H, m), 3.36–3.49 (5H, m), 3.67 (1H, d, J=2 Hz), 4.11 (1H, m), 4.2–4.3 (2H, m), 6.16 (1H, brd., J=9 Hz).

EXAMPLE 36

Ethyl (2S,3S)-3-[[1-(S)-hexyloxymethyl-3-methylbutyl]carbamoyl]oxirane-2-carboxylate (Compound No. 73)

The procedures similar to those of Example 1a were repeated to prepare the titled compound.

¹H-NMR (CDCl₃) δ: 0.89 (3H, t, J=7 Hz), 0.91 (6H, d, J=6 Hz), 1.31 (3H, t, J=7 Hz), 1.2–1.6 (11H, m), 3.37–3.43 (5H, m), 3.67 (1H, d, J=2 Hz), 4.12 (1H, m), 4.2–4.3 (2H, m), 6.16 (1H, brd, J=9 Hz).

EXAMPLE 37

Ethyl (2S,3S)-3-[[1-(S)-(cyclopropylmethoxy)methyl-3-ethylbutyl]carbamoyl]oxirane-2-carboxylate (Compound No. 74)

The procedures similar to those of Example 1a were repeated to prepare the titled compound.

¹H-NMR (CDCl₃) δ: 0.17–0.21 (2H, m), 0.50–0.55 (2H, m), 0.91 (3H, d, J=6 Hz), 0.92 (3H, d, J=6 Hz), 1.02 (1H, m), 1.32 (3H, t, J=7 Hz), 1.3–1.6 (3H, m), 3.26 (1H, dd, J=7,10 Hz), 3.30 (1H, dd, J=7,10 Hz), 3.43 (1H, d, J=2 Hz), 3.45 (2H, d, J=4 Hz), 3.67 (1H, d, J=2 Hz), 4.13 (1H, m), 4.2–4.3 (2H, m), 6.19 (1H, brd., J=9 Hz).

EXAMPLE 38

Ethyl (2S,3S)-3-[[1-(S)-(cyclohexylmethoxy)methyl-3-methylbutyl]carbamoyl]oxirane-2-carboxylate (Compound No. 75)

The procedures similar to those of Example 1a were repeated to prepare the titled compound.

¹H-NMR (CDCl₃) δ: 0.91 (6H, d, J=7 Hz), 1.32 (3H, t, J=7 Hz), 1.1–1.8 (14H, m), 3.15–3.25 (2H, m), 3.38 (2H, d, J=4 Hz), 3.43 (1H, d, J=2 Hz), 3.67 (1H, d, J=2 Hz), 4.12 (1H, m), 4.2–4.3 (2H, m), 6.15 (1H, brd., J=9 Hz).

EXAMPLE 39

Ethyl (2S,3S)-3-[[1-(S)-(2-methyl-2-propenyloxy)methyl-3-methylbutyl]carbamoyl]oxirane-2-carboxylate (Compound No. 76)

The procedures similar to those of Example 1a were repeated to prepare the titled compound.

¹-NMR (CDCl₃) δ: 0.91 (6H, d, J=6 Hz), 1.32 (3H, t, J=7 Hz), 1.72 (3H, s), 3.3–3.4 (2H, m), 3.43 (1H, d, J=2 Hz), 3.67 (1H, d, J=2 Hz), 3.85 (1H, d, J=13 Hz), 3.90 (1H, d, J=13 Hz), 4.1–4.2 (1H, m), 4.2–4.3 (2H, m), 4.90 (1H, m), 4.93 (1H, m), 6.18 (1H, brd., J=9 Hz).

EXAMPLE 40

Ethyl (2S,3S)-3-[[1-(S)-(2-methoxyethoxy)methyl-3-methylbutyl]carbamoyl]oxirane-2-carboxylate (Compound No. 78)

The procedures similar to those of Example 1a were repeated to prepare the titled compound.

¹H-NMR (CDCl₃) δ: 0.909 (3H, d, J=6 Hz), 0.912 (3H, d, J=6 Hz), 1.32 (3H, t, J=7 Hz), 1.3–1.5 (3H, m), 3.39 (3H, s), 3.43 (1H, d, J=2 Hz), 3.48–3–55 (4H, m), 3.59–3.62 (2H, m), 3.66 (1H, d, J=2 Hz), 4.13 (1H, m), 4.2–4.3 (2H, m), 6.26 (1H, brd., J=9 Hz).

EXAMPLE 41

Ethyl (2S,3S)-3-[[1-(S)-[(dimethylcarbamoyl)methoxy]methyl-3-methylbutyl]carbamoyl]oxirane-2- carboxylate (Compound No 79)

The procedures similar to those of Example 1a were repeated to prepare the titled compound.

m.p.: 64–65° C.; ¹H-NMR (CDCl₃) δ: 0.91 (3H, d, J=6 Hz), 0.92 (3H, d, J=6 Hz), 1.31 (3H, t, J=7 Hz), 1.3–1.6 (3H, m), 2.95 (3H, s), 2.96 (3H, s), 3.49 (1H, d, J=2 Hz), 3.50 (1H, dd, J=4,9 Hz), 3.61 (1H, dd, J=4,9 Hz), 3.67 (1H, d, J=2 Hz), 4.10 (1H, m), 4.16 (2H, s), 4.20–4.33 (2H, m), 7.01 (1H, brd., J=8 Hz).

EXAMPLE 42

Ethyl (2S,3S)-3-[[1-(S)-(4-diethylaminobutyloxy)methyl-3-methylbutyl]carbamoyl]oxirane-2-carboxylate (Compound No. 81)

The procedures similar to those of Example 1a were repeated to prepare the titled compound.

¹H-NMR (CDCl₃) δ: 0.91 (6H, d, J=6 Hz), 1.05 (6H, t, J=7 Hz), 1.31 (3H, t, J=7 Hz), 1.2–1.7 (7H, m), 2.4–2.7 (6H, m), 3.3–3.5 (5H, m), 3.67 (1H, d, J=2 Hz), 4.12 (1H, m), 4.20–4.33 (2H, m), 6.19 (1H, brd., J=8 Hz).

EXAMPLE 43

Isopropyl (2S,3S)-3-[[1-(S)-isobutoxymethyl-3-methylbutyl]carbamoyl]oxirane-2-carboxylate (Compound No. 82)

The procedures similar to those of Example 14 were repeated to prepare the titled compound.

m.p.: 36–38° C.; ¹H-NMR (CDCl₃) δ: 0.89 (6H, d, J=7 Hz), 0.91 (6H, d, J=7 Hz), 1.288 (3H, d, J=6 Hz), 1.293 (3H, d, J=6 Hz), 1.3–1.6 (3H, m), 1.85 (1H, m), 3.16 (1H, dd, J=7,9 Hz), 3.19 (1H, dd, J=7,9 Hz), 3.36–3.41 (3H, m), 3.39 (1H, d, J=4 Hz), 3.66 (1H, d, J=2 Hz), 4.12 (1H, m), 5.11 (1H, m), 6.18 (1H, brd., J=9 Hz).

EXAMPLE 44 tert-Butyl (2S,3S)-3-[[1-(S)-isobutoxymethyl-3-methylbutyl]carbamoyl]oxirane-2-carboxylate (Compound No. 83)

The procedures similar to those of Example 14 were repeated to prepare the titled compound.

m.p.: 73.5–74.5° C.; ¹H-NMR (CDCl₃) δ: 0.89 (6H, d, J=7 Hz), 0.91 (6H, d, J=7 Hz), 1.3–1.6 (3H, m), 1.49 (9H, s), 1.85 (1H, m), 3.15 (1H, dd, J=7,9 Hz), 3.19 (1H, dd, J=7,9 Hz), 3.31 (1H, d, J=2 Hz), 3.39 (1H, d, J=4 Hz), 3.61 (1H, d, J=2 Hz), 4.11 (1H, m), 4.20–4.33 (2H, m), 6.18 (1H, brd., J=9 Hz).

EXAMPLE 45

Cyclohexyl (2S,3S)-3-[[1-(S)-isobutoxymethyl-3-methylbutyl]carbamoyl]oxirane-2-carboxylate (Compound No. 84)

The procedures similar to those of Example 14 were repeated to prepare the titled compound.

¹H-NMR (CDCl₃) δ: 0.89 (6H, d, J7 Hz), 0.91 (6H, d, J=7 Hz), 1.2–1.6 (9H, m), 1.7–1.9 (5H, m), 3.16 (1H, dd, J=7,9 Hz), 3.19 (1H, dd, J=7,9 Hz), 3.38–3.43 (3H, m), 3.66 (1H, d, J=2 Hz), 4.12 (1H, m), 4.87 (1H, m), 6.19 (1H, brd., J=9 Hz).

EXAMPLE 46

Phenyl (2S,3S)-3-[[1-(S)-isobutoxymethyl-3-methylbutyl]carbamoyl]oxirane-2-carboxylate (Compound No. 85)

The procedures similar to those of Example 14 were repeated to prepare the titled compound.

¹H-NMR (CDCl₃) δ: 0.91 (6H, d, J=6 Hz), 0.94 (6H, d, J=6 Hz), 1.3–1.6 (3H, m), 1.87 (1H, m), 3.17 (1H, dd, J=7,9 Hz), 3.22 (1H, dd, J=7,9 Hz), 3.38–3.47 (2H, m), 3.67 (1H, d, J=2 Hz), 3.84 (1H, d, J=2 Hz), 4.15 (1H, m), 6.25 (1H, brd., J=9 Hz), 7.10–7.15 (2H, m), 7.27 (1H, m), 7.37–7.44 (2H, m).

EXAMPLE 47

4-tert-Butylphenyl (2S,3S)-3-[[1-(S)-isobutoxymethyl-3-methylbutyl]carbamoyl]oxirane-2-carboxylate (Compound No. 86)

The procedures similar to those of Example 14 were repeated to prepare the titled compound.

¹H-NMR (CDCl₃) δ: 0.91 (6H, d, J=6 Hz), 0.93 (6H, d, J=7 Hz), 1.32 (9H, s), 1.3–1.6 (3H, m), 1.87 (1H, m), 3.17 (1H, dd, J=6,9 Hz), 3.21 (1H, dd, J=7,9 Hz), 3.38–3.45 (2H, m), 3.66 (1H, d, J=2 Hz), 3.83 (1H, d, J=2 Hz), 4.15 (1H, m), 6.25 (1H, brd., J=9 Hz), 7.05 (2H, dm, J=9 Hz), 7.40 (2H, dm, J=9 Hz).

EXAMPLE 48

Sodium (2S,3S)-3-[[1-(S)-isobutoxymethyl-3-methylbutyl]carbamoyl]oxirane-2-carboxylate (Compound No. 87)

The procedures similar to those of Example 23 were repeated to prepare the titled compound.

¹H-NMR (D₂O) δ: 0.88 (6H, d, J=7 Hz), 0.88, 0.91 (6H, each d, J=7 Hz), 1.3–1.5 (2H, m), 1.59 (1H, m), 1.83 (1H, m), 3.27 (1H, dd, J=7,9 Hz), 3.34 (1H, dd, J=7,9 Hz), 3.41 (1H, d, J=2 Hz), 3.45 (1H, dd, J=8,11 Hz), 3.50–3.56 (2H, m, 4.16 (1H, m). IR (KBr) cm⁻¹: 3417, 3267, 3089, 2956, 2872, 1672, 1633, 1554, 1470, 1437, 1402, 1367, 1311, 1269, 1120, 1065, 962, 895, 862, 795, 769, 712, 673, 498.

EXAMPLE 49

Ethyl (2S,3S)-3-[[1-(S)-isobutoxymethyl-2-methylpropyl]carbamoyl]oxirane-2-carboxylate (Compound No. 88)

The procedures similar to those of Example 1a were repeated to prepare the titled compound.

m.p.: 40.5–45.0° C.; ¹H-NMR (CDCl₃) δ: 0 87 (3H, d, J=7 Hz), 0.89 (6H, d, J=7 Hz), 0.92 (3H, d, J=7 Hz), 1.32 (3H, t, J=7 Hz), 1.8–2.0 (2H, m), 3.14 (1H, dd, J=7,9 Hz), 3.18 (1H, dd, J7,9 Hz), 3.36 (1H, dd, J4,10 Hz), 3.46 (1H, d, J=2 Hz), 3.54 (1H, dd, J=4,10 Hz), 3.69 (1H, d, J=2 Hz), 3.78 (1H, m), 4.2–4.3 (2H, m), 6.31 (1H, brd., J=9 Hz). IR (KBr) cm⁻¹: 3417, 3255, 3076, 2958, 3873, 1755, 1674, 1655, 1558, 1475, 1466, 1387, 1369, 1346, 1286, 1261, 1227, 1198, 1146, 1113, 1038, 989, 895, 847, 744, 698, 663, 633.

EXAMPLE 50

Ethyl (2S,3S)-3-[[1-(S)-isobutoxymethyl-2-methylbutyl]carbamoyl]oxirane-2-carboxylate (Compound No. 89)

The procedures similar to those of Example 1a were repeated to prepare the titled compound.

¹H-NMR (CDCl₃) δ: 0.88 (3H, t, J=7 Hz), 0.89 (9H, d, J=7 Hz), 1.06 (1H, m), 1.32 (3H, t, J=7 Hz), 1.42 (1H, m), 1.66 (1H, s), 1.84 (1H, m), 3.14 (1H, dd, J=6,9 Hz), 3.18 (1H, dd, J=6,9 Hz), 3.37 (1H, dd, J=4,10 Hz), 3.45 (1H, d, J=2 Hz), 3.54 (1H, dd, J=4,10 Hz), 3.69 (1H, d, J=2 Hz), 3.85 (1H, m), 4.2–4.3 (2H, m), 6.32 (1H, brd., J=9 Hz).

EXAMPLE 51

Ethyl (2S,3S)-3-[[1-(S)-(hexanoylamino)methyl-3-methylbutyl]carbamoyl]oxirane-2-carboxylate (Compound No. 93)

The procedures similar to those of Example 1a were repeated to prepare the titled compound.

m.p.: 120–121° C.; ¹H-NMR (CDCl₃) δ: 0.83–0.95 (9H, m), 1.31 (3H, t, J=7 Hz), 1.2–1.4 (6H, m), 1.5–1.7 (3H, m), 3.2–3.4 (2H, m), 3.42 (1H, d, J=2 Hz), 3.65 (1H, d, J=2 Hz), 4.05 (1H, m), 4.20–4.35 (2H, m), 5.93 (1H, br.), 6.24 (1H, brd., J=9 Hz). IR (KBr) cm⁻¹: 3270, 2950, 2920, 1725, 1660, 1640, 1545, 14,65, 1370, 1300, 1275, 1215, 1025, 895.

EXAMPLE 52

Ethyl (2S,3S)-3-[[1-(S)-(N-benzyl-N-methylamino)methyl-3-methylbutyl]carbamoyl]oxirane-2-carboxylate (Compound No. 94)

The procedures similar to those of Example 1a were repeated to prepare the titled compound.

¹H-NMR (CDCl₃) δ: 0.89 (3H, d, J=6 Hz), 0.90 (3H, d, J=7 Hz), 1.32 (3H, t, J=7 Hz), 1.3–1.4 (2H, m), 1.53 (1H, m), 2.24 (3H, d), 2.30 (1H, dd, J=6,13 Hz), 2.36 (1H, dd, J=8,13 Hz), 3.40 (1H, d, J=2 Hz), 3.43 (1H, d, J=13 Hz), 3.57 (1H, d, J=13 Hz), 3.67 (1H, d, J=2 Hz), 4.07 (1H, m), 4.2–4.4 (2H, m), 5.93 (1H, brd., J=8 Hz), 7.2–7.4 (5H, m).

EXAMPLE 53

Ethyl (2S,3S)-3-[[1-(S)-(N-hexyl-N-methylamino)methyl-3-methylbutyl]carbamoyl]oxirane-2-carboxylate (Compound No. 95)

The procedures similar to those of Example 1a were repeated to prepare the titled compound.

¹H-NMR (CDCl₃) δ: 0.89 (3H, t, J=7 Hz), 0.90 (3H, d, J=6 Hz), 0.91 (3H, d, J=7 Hz), 1.31 (3H, t, J=7 Hz), 1.2–1.6 (11H, m), 2.21 (3H, s), 2.25–2.40 (4H, m), 3.42 (1H, d, J=2 Hz), 3.65 (1H, d, J=2 Hz), 3.99 (1H, m), 4.2–4.3 (2H, m), 6.05 (1H, brd, J=7 Hz).

REFERENCE EXAMPLE 1

(1R,2S)-2-amino-3-methyl-1-phenyl-1-pentanol (Starting compound of Example 3)

1) To a stirred suspension of phosphorus pentachloride (31.4 g, 0.151 mmol.) in anhydrous benzene (300 mL) was added L-isoleucine (19.67 g, 0.151 mmol.) under chilling with ice. The mixture was then stirred for 2 hours under chilling with ice, and further stirred for 17 hours at room temperature. The reaction mixture was chilled with ice and anhydrous aluminum chloride (60 g) was portionwise added. The mixture was then slowly heated to reflux temperature for a period of 2 hours. The mixture was refluxed for 3 hours, and then chilled with ice. The chilled reaction mixture was slowly added to a mixture of concentrated hydrochloric acid (45 mL) and ice (0.3 kg). The resulting mixture was stirred at 5° C. for 40 min. The precipitated crystals were collected by filtration and washed with benzene The washed crystals were dried in air to give 2-(S)-amino-3-methyl-1-phenyl-1-pentanone hydrochloride as a white crystalline product (29.2 g, yield: 85%).

2) The 2-(S)-amino-3-methyl-1-phenyl-1-pentanone hydrochloride (24.2 g, 0.106 mmol.) prepared above was dissolved in methanol (250 mL). The solution was stirred under chilling with ice to maintain the solution temperature at a temperature of lower than 10° C., and to this was portionwise added sodium borohydride (3.8 g, 0.10 mmol.). The reaction mixture was stirred for one hour at the same temperature, and concentrated under reduced pressure. To the residue were added chloroform (100 mL), water (50 mL), and 2N aqueous sodium hydroxide solution. The chloroform layer was separated, and the aqueous layer was subjected to extraction using chloroform. The chloroform portions were combined, successively washed with water and aqueous saturated sodium chloride solution, and dried over anhydrous sodium sulfate. The solvent was distilled off under reduced pressure, to give the titled compound as a white crystalline product (17.8 g, yield: 87%).

$^1$H-NMR (CDCl$_3$) δ: 0.87 (3H, t, J=7 Hz), 1.01 (3H, d, J=7 Hz), 1.13 (1H, m), 1.38 (1H, m), 1.56 (1H, m), 2.81 (1H, t, J=6 Hz), 4.68 (1H, d, J=6 Hz), 7.25–7.38 (5H, m).

REFERENCE EXAMPLE 2

1-(S)-[α-(R)-methoxybenzyl]-3-methylbutylamine
(Starting compound of Example 5)

1) To a solution of N-[1-(S)-[α-(R)-hydroxybenzyl]-3-methylbutyl]phthalimide (30.4 g, 94.0 mmol.) in toluene (380 mL) were successively added methyl p-toluenesulfonate (19.2 g, 103 mmol.) and 60% sodium hydride (4.13 g, 103 mmol.). The resulting mixture was heated under reflux for 18 hours under stirring, cooled to room temperature, successively washed with water and aqueous saturated sodium chloride solution, dried over anhydrous sodium sulfate. The solvent was distilled off under reduced pressure. The residue was purified by middle pressure column chromatography (n-hexane/ethyl acetate= 5/1), to give N-[1-(S)-[α-(R)-methoxybenzyl]-3-methylbutyl]phthalimide as a white crystalline product (25.6 g, yield: 81%).

2) The N-[1-(S)-[α-(R)-methoxybenzyl]-3-methylbutyl] phthalimide (25.6 g, 75.9 mmol.) obtained above was suspended in ethanol (250 mL). To the suspension was added hydrazine hydrate (7.5 mL), and the resulting mixture was heated under reflux for 15 hours. The reaction mixture was chilled in an ice bath, and stirred at 5° C. for one hour after addition of 4N hydrochloric acid (200 mL). The insoluble material was removed by filtration and washed with 4N hydrochloric acid. The filtrate and washings were combined, and placed under reduced pressure to distill off ethanol. The residue was made basic to reach pH approx. 11, by addition of 10N aqueous sodium hydroxide solution, and extracted with chloroform. The extract was washed with aqueous saturated sodium chloride solution and dried over anhydrous sodium sulfate. The dried extract was placed under reduced pressure to give the titled compound as pale yellow oil (15.5 g, purity: 91%, yield: 81%).

$^1$H-NMR (CDCl$_3$) δ: 0.86 (3H, d, J=6 Hz), 0.91 (3H, d, J=6 Hz), 1.03 (2H, brs.), 1.06 (1H, ddd, J=14,10,4 Hz), 1.34 (1H, ddd, J=14,10,3 Hz), 1.76 (1H, m), 3.06 (1H, ddd, J=10,5,3 Hz), 3.24 (3H, s), 3.96 (1H, d, J=5 Hz), 7.26–7.39 (5H, m).

REFERENCE EXAMPLE 3

1-(S)-(diphenylmethoxy)methyl-3-methylbutylamine
(Starting compound of Example 21)

To a solution of (S)-(+)-leucinol (118 mg, 1.0 mmol.) in toluene (8 mL) were successively added methanesulfonic acid (96 mg., 1.0 mmol.) and tris(diphenylmethyl)phosphate (0.60 g, 1.0 mmol.) The resulting mixture was heated under reflux for 30 minutes, cooled to room temperature, poured into aqueous 10 sodium carbonate solution, and extracted with ethyl acetate. The extract was successively washed with water and aqueous saturated sodium chloride solution, and dried over anhydrous sodium sulfate. The dried extract was placed under reduced pressure to distill off the solvent. To the residue was added chloroform (10 mL), and the insoluble material was removed by filtration. The filtrate was placed under reduced pressure. The residue was dissolved in ether (2 mL) The solution was added to a solution of oxalic acid dihydrate (0.14 g) in methanol (2 mL) with stirring. The mixture was allowed to stand overnight. The precipitate crystals were collected by filtration, washed with a mixture of methanol and ether (1/1), and dried. The obtained oxalate was treated with aqueous sodium hydroxide solution to give the titled compound as pale yellow oil (126 mg, yield: 44%).

$^1$H-NMR (CDCl$_3$) δ: 0.88 (3H, d, J=6 Hz), 0.89 (3H, d, J=6 Hz), 1.16–1.28 (2H, m), 1.68 (1H, m), 1.98 (2H, br), 3.11 (1H, m), 3.22 (1H, dd, J=9,8 Hz), 3.43 (1H, dd, J=9,4 Hz), 5.35 (1H, s), 7.21–7.37 (10H, m).

PHARMACOLOGICAL EXPERIMENT 1

Evaluation on Bone Resorption Inhibitory Activity
(by index of decrease of plasma calcium concentration in rats grown with low calcium feed)

(1) If rats are grown with low calcium feed, its bone weight decreases This is because calcium is left from bone by dissolution in blood (i.e., bone resorption) so as to maintain the calcium concentration in blood at a normal level. Therefore, compounds inhibiting bone resorption in the model adopted in this experiment inhibit dissolution of calcium in blood from bone to reduce the plasma calcium concentration. Thus, compounds of the invention were evaluated in their bone resorption inhibitory activity by measuring decrease of plasma calcium concentration in the following experiment (according to J. M. Delaisse et al., Biochem. Biophys, Res. Commun., 125, 441 (1984).

(2) Experimental procedures

Rats of Wistar strain (age: 5 to 6 weeks) were grown with a low calcium content feed (Ca: 0.02%, available from Oriental Yeast Industries, Co., Ltd.) for one week to give bone resorption-enhanced condition. A test compound was dissolved in aqueous 1% methylcellulose solution (when the test compound was hydrophobic, Tween 20, nonionic surfactant, was added), and administered orally to the rat in a dosage of 0.2 mL/100 g (weight of rat). At 6 hours after the administration, blood was taken from tail vein of the rat. Then, the plasma calcium concentration was measured by OCPC method.

The plasma calcium concentration decreasing activity (Ca decrease rate) of the test compound was calculated by the following equation:

Ca decrease rate (%)=100×[plasma calcium concentration at 6 hours after administration of test compound)−(plasma calcium concentration at the same time in non-administration group)/ (plasma calcium concentration at the same time in non-administration group)

(3) Experimental results

The results are set forth in Table 2 (in which the test compound is indicated by the number of the aforementioned Example). The results teach that the epoxysuccinamide compounds of the invention decrease plasma calcium concentration and therefore inhibit enhanced bone resorption.

TABLE 2

| Test Compound | Dose (mg/kg, p.o.) | Measured Plasma Ca Concentration |
|---|---|---|
| Example 1a | 15 | −12.5% |
| Example 5 | 15 | −20.4% |
| Example 7 | 15 | −13.6% |
| Example 8 | 15 | −15.8% |
| Example 11 | 15 | −17.3% |
| Example 13 | 15 | −14.7% |
| Example 14 | 5 | −9.9% |
| Example 17 | 15 | −15.4% |
| Example 18a | 15 | −24.5% |

PHARMACOLOGICAL EXPERIMENT 2

Cathepsin L Inhibitory Action (1) Preparation of Rat Liver Lysosome Fraction

Male rat of Wistar strain was killed by exsanguination and a ice-chilled physiological saline was introduced into portal vein for circulation. Then, its liver was taken out. Thereafter, the following procedures were performed at 4° C.

The liver was minced by scissors. Five grams of minced liver were homogenized in a Potter type Teflon Homogenizer after addition of 9 volumes of 0.25 M sucrose. The homogenate was centrifuged at 800 G for 10 minutes. The resulting supernatant was further centrifuged at 12,000 G for 20 minutes. The precipitate was homogenized in 25 mL of 0.25 M sucrose, and then centrifuged at 12,000 G for 20 minutes. The resulting precipitate was further homogenized in 10 mL of 0.25 M sucrose. Thus, a lysosome fraction was obtained The lysosome fraction was diluted with 0.25M sucrose containing 0.33% of Triton X-100 for the use in the measurement of cathepsin L activity.

(2) Measurement of Cathepsin L Activity

To 0.25 mL of a solution (pH: 5.5) containing 340 mM sodium acetate, 60 mM acetic acid, 4 mM EDTA and 8 mM dithiothreitol were added 0.1 mL of the lysosome fraction, 5 μL of the test compound solution, and 0.545 mL of distilled water. The mixture was pre-incubated at 30° C. for 15 minutes. Thereafter, 0.1 mL of 50 μM carbobenzoxy-L-phenylalanyl-L-arginine-4-methylcoumaryl-7-amide (Z-Phe-Arg-MCA) solution was added, and the reaction was started. The reaction was performed at 30° C. for 20 minutes, and then terminated by addition of 1 mL of an aqueous solution (pH: 4.3) containing 100 mM sodium monochloroacetate, 30 mM sodium acetate and 70 mM acetic acid. The finally obtained solution was subjected to measurement of fluorescence strength (excitation wavelength: 380 nm, emission wavelength: 460 nm).

The Z-Phe-Arg-MCA is also decomposed by cathepsin B which is contained in the lysosome fraction. Therefore, the measurement was performed in the presence of $10^{-7}$ M CA-074 (Murata et al., FEBS Lett., 280, 307–310 (1991)] which was known as a cathepsin B specific inhibitor, so that the cathepsin B activity was completely inhibited.

(3) Results of Measurement

The results of the measurement are set forth in the following Table 3 (in which the test compound is indicated by the number of the aforementioned Example).

PHARMACOLOGICAL EXPERIMENT 3

Cathepsin B Inhibitory Action (1) Measuring Procedures

To 0.25 mL of a solution (pH: 6.0) containing 352 mM $KH_2O_4$, 48 mM $Na_2HPO_4$, 5.32 mM EDTA.2Na and 10 mM L-cysteine were added 0.1 mL of the lysosome fraction, 5 μL of the test compound solution, and 0.545 mL of distilled water. The mixture was pre-incubated at 30° C. for 15 minutes. Thereafter, the reaction was started by the addition of 0.1 mL of a solution of 50 μM carbobenzoxy-L-arginine-L-arginine-4-methylcoumaryl-7-amide (Z-Arg-Arg-MCA, substrate). The reaction was performed at 30° C. for 20 minutes, and then terminated by addition of 1 mL of an aqueous solution (pH: 4.3) containing 100 mM sodium monochloroacetate, 30 mM sodium acetate and 70 mM acetic acid. The finally obtained solution was subjected to measurement of fluorescence strength (excitation wavelength: 380 nm, emission wavelength: 460 nm).

(2) Results of Measurement

The results of the measurement are set forth in the following Table 3(in which the test compound is indicated by the number of the aforementioned Example).

TABLE 3

| | Cathepsin Inhibition ($IC_{50}$) | |
|---|---|---|
| Test Compound | Cathepsin L | Cathepsin B |
| Example 2 | $1.1 \times 10^{-8}$ | $1.2 \times 10^{-7}$ |
| Example 9 | $5.7 \times 10^{-8}$ | $2.1 \times 10^{-7}$ |
| Example 11 | $1.8 \times 10^{-8}$ | $8.5 \times 10^{-8}$ |
| Example 12 | $9.4 \times 10^{-8}$ | $1.0 \times 10^{-7}$ |
| Example 22 | $3.3 \times 10^{-9}$ | $4.1 \times 10^{-8}$ |
| Example 23 | $1.1 \times 10^{-8}$ | — |
| Example 24 | $6.9 \times 10^{-9}$ | $2.8 \times 10^{-8}$ |

The above results indicate that the epoxysuccinamide derivative of the invention has a cathepsin B inhibitory action in addition to the cathepsin L inhibitory action.

PHARMACOLOGICAL EXPERIMENT 4

Action on Ovariectomized Rats (1) Experimental Model

The ovariectomized rats were employed as models of postmenopausal osteoporosis, for evaluating the compound of the invention.

(2) Experimental Procedures

The ovaries on both sides were removed surgically in SD female rats (age: 13 weeks). From the next day, a test compound (compound of Example 5) was administered at 300 mg/kg to the rats once a day for 4 weeks (administration group: 8 rats). After the last administration was complete, the fourth vertebrae lumbale was taken out, and the total bone density was measured by means of p-QCT (Peripheral Bone Density-Measuring Apparatus) and compared with the bone density of the control group (7 rats). In addition, rats treated by false-operation were also subjected to the sane measurement.

(3) Results of Experiment

The results are set forth in Table 4. The results indicate that the epoxysuccinamide derivative of the invention inhibits decrease of bone density caused by ovariectomy and therefore is effective in treating osteoporosis.

TABLE 4

| Group | Total bone density (mg/cm³) of the fourth vertebrae lumbale |
| --- | --- |
| False Operation Group | 658.8 ± 46.3 |
| Control Group | 543.7 ± 31.4 |
| Administration Group | 617.8 ± 37.9** |

Average value ± Standard Deviation: **P < 0.01 (vs. Control Group)

PHARMACOLOGICAL EXPERIMENT 5

Action on Rat Adjuvant Arthritis (1) Experimental Model

Rat adjuvant arthritis which is considered as a model of rheumatoid arthritis of human being was employed for evaluation of the compound of the invention.

(2) Experimental Procedures

Male rats of Wistar strain (age: 5 weeks) were sensitized by subcutaneous injection of Mycobacterium Butyricum which was suspended in liquid paraffin into the right hind paw. From the next day, a test compound (the compound of the aforementioned Example 5) was orally administered at a dosage of 300 mg/kg once a day for 21 days (administration group: 8 rats). After the last administration was complete, a volume of the untreated hind paw was measured by means of Volume Differential Meter and compared with that of Control group (8 rats, non-administration group). In addition, a non-adjuvant treatment group (normal groups 8 rats) was subjected to the same measurement. Inhibition of expansion of the hind paw by the test compound (Inhibition rate) was calculated by the following equation:

Inhibition rate (%)=100×(administration group−control group)/(normal group−control group)

(3) Results of Experiment

The test compound inhibits the expansion of the hind paw by 42% (which is significant, in comparison with the control group, with a risk of <1%, according to Mann-Whitney' U test).

This result indicates that the epoxysuccinamide derivative of the invention is effective in treating rheumatoid arthritis.

We claim:

1. An epoxysuccinamide derivative having the following formula (1) and its physiologically acceptable salt:

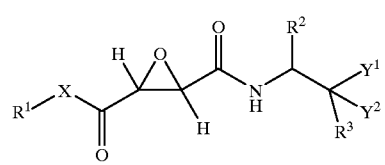

(1)

wherein $R^1$ represents a hydrogen atom, an alkyl group having 1 to 10 carbon atoms, an alkenyl group having 2 to 10 carbon atoms, an alkynyl group having 2 to 10 carbon atoms, an aryl group having 6 to 20 carbon atoms, or an aralkyl group consisting of an aryl group having 6 to 20 carbon atoms and an alkyl group having 1 to 6 carbon atoms;

$R^2$ represents an alkyl group having 1 to 10 carbon atoms, an alkenyl group having 2 to 10 carbon atoms, an alkynyl group having 2 to 10 carbon atoms, an aryl group having 6 to 20 carbon atoms, or an aralkyl group consisting of an aryl group having 6 to 20 carbon atoms and an alkyl group having 1 to 6 carbon atoms;

$R^3$ represents a hydrogen atom, an alkyl group having 1 to 10 carbon atoms, an alkenyl group having 2 to 10 carbon atoms, an alkynyl group having 2 to 10 carbon atoms, an aryl group having 6 to 20 carbon atoms, an aralkyl group consisting of an aryl group having 6 to 20 carbon atoms and an alkyl group having 1 to 6 carbon atoms, a heterocyclic group having 3 to 12 carbon atoms, or a heterocyclic-alkyl group consisting of a heterocyclic group having 3 to 12 carbon atoms and an alkyl group having 1 to 6 carbon atoms;

X represents —O— or —$NR^4$— in which $R^4$ is a hydrogen atom, an alkyl group having 1 to 10 carbon atoms, an aryl group having 6 to 20 carbon atoms, an aralkyl group consisting of an aryl group having 6 to 20 carbon atoms and an alkyl group having 1 to 6 carbon atoms, a heterocyclic group having 3 to 12 carbon atoms, or a heterocyclic-alkyl group consisting of a heterocyclic group having 3 to 12 carbon atoms and an alkyl group having 1 to 6 carbon atoms;

$Y^1$ represents a hydroxyl group, an alkoxy group having 1 to 6 carbon atoms, an acetoxy group, or an aralkyloxy group consisting of an aryl group having 6 to 20 carbon atoms and an alkyl group having 1 to 6 carbon atoms; and $Y^2$ represents a hydrogen atom or an alkyl group having 1 to 10 carbon atoms;

provided that the aryl group for $R^1$ to $R^4$ may have one or more substituents selected from the group consisting of alkyl having 1–6 carbon atoms, hydroxyl, amino, alkylamino having 1–6 carbon atoms, dialkylamino having 2–12 carbon atoms in total, alkoxy having 1–6 carbon atoms, halogen, haloalkyl having 1–6 carbon atoms, cyano, nitro, carboxyl, alkoxy-carbonyl having 2–7 carbon atoms, —$CONH_2$, alkylaminocarbonyl having 2–7 carbon atoms, dialkylaminocarbonyl having 3–13 carbon atoms in total, amidino, and guanidino; and provided that the heterocyclic group for $R^3$ and $R^4$ is selected from the group consisting of pyridyl, pyrrolidinyl, piperidinyl, furyl, thienyl, piperazinyl, indolyl and benzimidazolyl.

2. The epoxysuccinamide derivative of the formula (1) and its physiologically acceptable salt defined in claim 1, wherein $R^1$ is a hydrogen atom or an alkyl group having 1 to 6 carbon atoms.

3. The epoxysuccinamide derivative of the formula (1) and its physiologically acceptable salt defined in claim 1, wherein $R^2$ is an alkyl group having 1 to 6 carbon atoms, phenyl, or benzyl.

4. The epoxysuccinamide derivative of the formula (1) and its physiologically acceptable salt defined in claim 1, wherein $R^3$ is a hydrogen atom or an aryl group having 6 to 20 carbon atoms.

5. The epoxysuccinamide derivative of the formula (1) and its physiologically acceptable salt defined in claim 1, wherein X is —O—.

6. The physiologically acceptable salt of the epoxysuccinamide derivative defined in claim 1, wherein the physiologically acceptable salt is an alkali metal salt.

7. An epoxysuccinamide derivative having the following formula (1) and its physiologically acceptable salt:

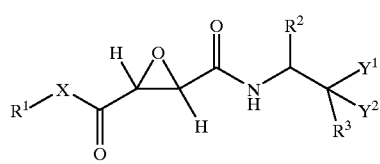

wherein
R¹ represents a hydrogen atom, an alkyl group having 1 to 10 carbon atoms, an alkenyl group having 2 to 10 carbon atoms, an alkynyl group having 2 to 10 carbon atoms, an aryl group having 6 to 20 carbon atoms, or an aralkyl group consisting of an aryl group having 6 to 20 carbon atoms and an alkyl group having 1 to 6 carbon atoms;

R² represents an isobutyl group or an isopropyl group;

R³ represents a hydrogen atom or an aryl group having 6 to 20 carbon atoms;

X represents —O— or —NR⁴— in which R⁴ is a hydrogen atom, an alkyl group having 1 to 10 carbon atoms, an aryl group having 6 to 20 carbon atoms, an aralkyl group consisting of an aryl group having 6 to 20 carbon atoms and an alkyl group having 1 to 6 carbon atoms, a heterocyclic group having 3 to 12 carbon atoms, or a heterocyclic-alkyl group consisting of a heterocyclic group having 3 to 12 carbon atoms and an alkyl group having 1 to 6 carbon atoms;

Y¹ represents OR⁵ in which R⁵ is a hydrogen atom, an alkyl group having 1 to 10 carbon atoms, an aryl group having 6 to 20 carbon atoms, an aralkyl group consisting of an aryl group having 6 to 20 carbon atoms and an alkyl group having 1 to 6 carbon atoms, an acetoxy group, a benzoyloxy group, a heterocyclic group having 3 to 12 carbon atoms, or a heterocyclic-alkyl group consisting of a heterocyclic group having 3 to 12 carbon atoms and an alkyl group having 1 to 6 carbon atoms; and Y² represents a hydrogen atom;

provided that the alkyl group for R⁵ may have one or more substituents selected from the group consisting of hydroxyl, amino, alkylamino having 1–6 carbon atoms, dialkylamino having 2–12 carbon atoms in total, alkoxy having 1–6 carbon atoms, carboxyl, alkoxycarbonyl having 2–7 carbon atoms, —CONH₂, alkylaminocarbonyl having 2–7 carbon atoms, dialkylaminocarbonyl having 3–13 carbon atoms in total, and guanidino; provided that the aryl group for R¹, R³ and R⁵ may have one or more substituents selected from the group consisting of alkyl having 1–6 carbon atoms, hydroxyl, amino, alkylamino having 1–6 carbon atoms, dialkylamino having 2–12 carbon atoms in total, alkoxy having 1–6 carbon atoms, halogen, haloalkyl having 1–6 carbon atoms, cyano, nitro, carboxyl, alkoxycarbonyl having 2–7 carbon atoms, —CONH₂, alkylaminocarbonyl having 2–7 carbon atoms, dialkylaminocarbonyl having 3–13 carbon atoms in total, amidino, and guanidino;

provided that the heterocyclic group for R⁵ may have one or more substituents selected from the group consisting of alkyl having 1–6 carbon atoms, hydroxyl, amino, alkylamino having 1–6 carbon atoms, dialkylamino having 2–12 carbon atoms in total, alkoxy having 1–6 carbon atoms, halogen, haloalkyl having 1–6 carbon atoms, cyano, nitro, carboxyl, alkoxycarbonyl having 2–7 carbon atoms, —CONH₂, alkylaminocarbonyl having 2–7 carbon atoms, dialkylaminocarbonyl having 3–13 carbon atoms in total, amidino, and guanidino; and provided that the heterocyclic group for R³, R⁴ and R⁵ is selected from the group consisting of pyridyl, pyrrolidinyl, piperidinyl, furyl, thienyl, piperazinyl, indolyl and benzimidazolyl.

8. The epoxysuccinamide derivative of the formula (1) and its physiologically acceptable salt defined in claim 7, wherein R¹ is a hydrogen atom or an alkyl group having 1 to 6 carbon atoms.

9. The epoxysuccinamide derivative of the formula (1) and its physiologically acceptable salt defined in claim 7, wherein X is —O—.

10. The physiologically acceptable salt of the epoxysuccinamide derivative defined in claim 7, wherein the physiologically acceptable salt is an alkali metal salt.

11. An epoxysuccinamide derivative selected from the group consisting of the following compounds and its physiologically acceptable salt:

ethyl (2S,3S)-3-[[1-(S)-benzoyl-3-methylbutyl]carbamoyl]oxirane-2-carboxylate;

ethyl (2S,3s)-3-[[1-(S)-benzoyl-2-methylpropyl]carbamoyl]oxirane-2-carboxylate; and ethyl (2S,3S)-3-[[1-(S)-(2-methyl-2-propenyloxy)methyl-3-methylbutyl]carbamoyl]oxirane-2-carboxylate.

12. A method for treating a bone disease selected from the group consisting of osteoporosis, malignant hypercalcemia and Paget's disease, the method comprising injecting or orally administering into a patient an epoxysuccinamide derivative having the following formula (1) and its physiologically acceptable salt in an amount of 0.01 to 100 mg/day in the case of injection or in an amount of 0.1 mg/day to 1 g/day in the case of oral administration:

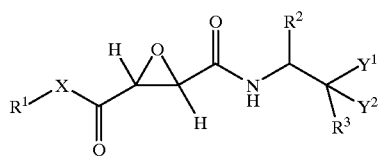

wherein
R¹ represents a hydrogen atom, an alkyl group having 1 to 10 carbon atoms, an alkenyl group having 2 to 10 carbon atoms, an alkynyl group having 2 to 10 carbon atoms, an aryl group having 6 to 20 carbon atoms, or an aralkyl group consisting of an aryl group having 6 to 20 carbon atoms and an alkyl group having 1 to 6 carbon atoms;

R² represents an alkyl group having 1 to 10 carbon atoms, an alkenyl group having 2 to 10 carbon atoms, an alkynyl group having 2 to 10 carbon atoms, an aryl group having 6 to 20 carbon atoms, or an aralkyl group consisting of an aryl group having 6 to 20 carbon atoms and an alkyl group having 1 to 6 carbon atoms;

R³ represents a hydrogen atom, an alkyl group having 1 to 10 carbon atoms, an alkenyl group having 2 to 10 carbon atoms, an alkynyl group having 2 to 10 carbon atoms, an aryl group having 6 to 20 carbon atoms, an aralkyl group consisting of an aryl group having 6 to 20 carbon atoms and an alkyl group having 1 to 6 carbon atoms, a heterocyclic group having 3 to 12 carbon atoms, or a heterocyclic-alkyl group consisting of a heterocyclic group having 3 to 12 carbon atoms and an alkyl group having 1 to 6 carbon atoms;

X represents —O— or —$NR^4$— in which $R^4$ is a hydrogen atom, an alkyl group having 1 to 10 carbon atoms, an aryl group having 6 to 20 carbon atoms, an aralkyl group consisting of an aryl group having 6 to 20 carbon atoms and an alkyl group having 1 to 6 carbon atoms, a heterocyclic group having 3 to 12 carbon atoms, or a heterocyclic-alkyl group consisting of a heterocyclic group having 3 to 12 carbon atoms and an alkyl group having 1 to 6 carbon atoms;

$Y^1$ represents a hydroxyl group, an alkoxy group having 1 to 6 carbon atoms, an acetoxy group, or an aralkyloxy group consisting of an aryl group having 6 to 20 carbon atoms and an alkyl group having 1 to 6 carbon atoms; and $Y^2$ represents a hydrogen atom or an alkyl group having 1 to 10 carbon atoms;

provided that the aryl group for $R^1$ to $R^4$ may have one or more substituents selected from the group consisting of alkyl having 1–6 carbon atoms, hydroxyl, amino, alkylamino having 1–6 carbon atoms, dialkylamino having 2–12 carbon atoms in total, alkoxy having 1–6 carbon atoms, halogen, haloalkyl having 1–6 carbon atoms, cyano, nitro, carboxyl, alkoxycarbonyl having 2–7 carbon atoms, —$CONH_2$, alkylaminocarbonyl having 2–7 carbon atoms, dialkylaminocarbonyl having 3–13 carbon atoms in total, amidino, and guanidino; and provided that the heterocyclic group for $R^3$ and $R^4$ is selected from the group consisting of pyridyl, pyrrolidinyl, piperidinyl, furyl, thienyl, piperazinyl, indolyl and benzimidazolyl.

13. A method for treating arthritis which comprises injecting or orally administering into a patient an epoxysuccinamide derivative having the following formula (1) and its physiologically acceptable salt in an amount of 0.01 to 100 mg/day in the case of injection or in an amount of 0.1 mg/day to 1 g/day in the case of oral administration:

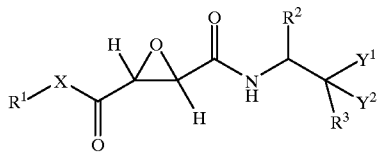

(1)

wherein $R^1$ represents a hydrogen atom, an alkyl group having 1 to 10 carbon atoms, an alkenyl group having 2 to 10 carbon atoms, an alkynyl group having 2 to 10 carbon atoms, an aryl group having 6 to 20 carbon atoms, or an aralkyl group consisting of an aryl group having 6 to 20 carbon atoms and an alkyl group having 1 to 6 carbon atoms;

$R^2$ represents an alkyl group having 1 to 10 carbon atoms, an alkenyl group having 2 to 10 carbon atoms, an alkynyl group having 2 to 10 carbon atoms, an aryl group having 6 to 20 carbon atoms, or an aralkyl group consisting of an aryl group having 6 to 20 carbon atoms and an alkyl group having 1 to 6 carbon atoms;

$R^3$ represents a hydrogen atom, an alkyl group having 1 to 10 carbon atoms, an alkenyl group having 2 to 10 carbon atoms, an alkynyl group having 2 to 10 carbon atoms, an aryl group having 6 to 20 carbon atoms, an aralkyl group consisting of an aryl group having 6 to 20 carbon atoms and an alkyl group having 1 to 6 carbon atoms, a heterocyclic group having 3 to 12 carbon atoms, or a heterocyclic-alkyl group consisting of a heterocyclic group having 3 to 12 carbon atoms and an alkyl group having 1 to 6 carbon atoms;

X represents —O— or —$NR^4$— in which $R^4$ is a hydrogen atom, an alkyl group having 1 to 10 carbon atoms, an aryl group having 6 to 20 carbon atoms, an aralkyl group consisting of an aryl group having 6 to 20 carbon atoms and an alkyl group having 1 to 6 carbon atoms, a heterocyclic group having 3 to 12 carbon atoms, or a heterocyclic-alkyl group consisting of a heterocyclic group having 3 to 12 carbon atoms and an alkyl group having 1 to 6 carbon atoms;

$Y^1$ represents a hydroxyl group, an alkoxy group having 1 to 6 carbon atoms, an acetoxy group, or an aralkyloxy group consisting of an aryl group having 6 to 20 carbon atoms and an alkyl group having 1 to 6 carbon atoms; and $Y^2$ represents a hydrogen atom or an alkyl group having 1 to 10 carbon atoms;

provided that the aryl group for $R^1$ to $R^4$ may have one or more substituents selected from the group consisting of alkyl having 1–6 carbon atoms, hydroxyl, amino, alkylamino having 1–6 carbon atoms, dialkylamino having 2–12 carbon atoms in total, alkoxy having 1–6 carbon atoms, halogen, haloalkyl having 1–6 carbon atoms, cyano, nitro, carboxyl, alkoxy-carbonyl having 2–7 carbon atoms, —$CONH_2$, alkylamino-carbonyl having 2–7 carbon atoms, dialkylaminocarbonyl having 3–13 carbon atoms in total, amidino, and guanidino; and provided that the heterocyclic group for $R^3$ and $R^4$ is selected from the group consisting of pyridyl, pyrrolidinyl, piperidinyl, furyl, thienyl, piperazinyl, indolyl and benzimidazolyl.

14. A method for treating a bone disease selected from the group consisting of osteoporosis, malignant hypercalcemia and Paget's disease, the method comprising injecting or orally administering into a patient an epoxysuccinamide derivative having the following formula (1) and its physiologically acceptable salt in an amount of 0.01 to 100 mg/day in the case of injection or in an amount of 0.1 mg/day to 1 g/day in the case of oral administration:

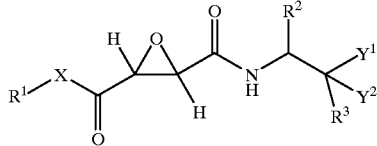

(1)

wherein $R^1$ represents a hydrogen atom, an alkyl group having 1 to 10 carbon atoms, an alkenyl group having 2 to 10 carbon atoms, an alkynyl group having 2 to 10 carbon atoms, an aryl group having 6 to 20 carbon atoms, or an aralkyl group consisting of an aryl group having 6 to 20 carbon atoms and an alkyl group having 1 to 6 carbon atoms;

$R^2$ represents an isobutyl group or an isopropyl group;

$R^3$ represents a hydrogen atom or an aryl group having 6 to 20 carbon atoms;

X represents —O— or —NR⁴— in which R⁴ is a hydrogen atom, an alkyl group having 1 to 10 carbon atoms, an aryl group having 6 to 20 carbon atoms, an aralkyl group consisting of an aryl group having 6 to 20 carbon atoms and an alkyl group having 1 to 6 carbon atoms, a heterocyclic group having 3 to 12 carbon atoms, or a heterocyclic-alkyl group consisting of a heterocyclic group having 3 to 12 carbon atoms and an alkyl group having 1 to 6 carbon atoms;

$Y^1$ represents $OR^5$ in which $R^5$ is a hydrogen atom, an alkyl group having 1 to 10 carbon atoms, an aryl group having 6 to 20 carbon atoms, an aralkyl group consisting of an aryl group having 6 to 20 carbon atoms and an alkyl group having 1 to 6 carbon atoms, an acetoxy group, a benzoyloxy group, a heterocyclic group having 3 to 12 carbon atoms, or a heterocyclic-alkyl group consisting of a heterocyclic group having 3 to 12 carbon atoms and an alkyl group having 1 to 6 carbon atoms; and $Y^2$ represents a hydrogen atom;

provided that the alkyl group for $R^5$ may have one or more substituents selected from the group consisting of hydroxyl, amino, alkylamino having 1–6 carbon atoms, dialkylamino having 2–12 carbon atoms in total, alkoxy having 1–6 carbon atoms, carboxyl, alkoxycarbonyl having 2–7 carbon atoms, —CONH₂, alkylaminocarbonyl having 2–7 carbon atoms, dialkylaminocarbonyl having 3–13 carbon atoms in total, and guanidino;

provided that the aryl group for $R^1$, $R^3$ and $R^5$ may have one or more substituents selected from the group consisting of alkyl having 1–6 carbon atoms, hydroxyl, amino, alkylamino having 1–6 carbon atoms, dialkylamino having 2–12 carbon atoms in total, alkoxy having 1–6 carbon atoms, halogen, haloalkyl having 1–6 carbon atoms, cyano, nitro, carboxyl, alkoxycarbonyl having 2–7 carbon atoms, —CONH₂, alkylaminocarbonyl having 2–7 carbon atoms, dialkylaminocarbonyl having 3–13 carbon atoms in total, amidino, and guanidino;

provided that the heterocyclic group for $R^5$ may have one or more substituents selected from the group consisting of alkyl having 1–6 carbon atoms, hydroxyl, amino, alkylamino having 1–6 carbon atoms, dialkylamino having 2–12 carbon atoms in total, alkoxy having 1–6 carbon atoms, halogen, haloalkyl having 1–6 carbon atoms, cyano, nitro, carboxyl, alkoxycarbonyl having 2–7 carbon atoms, —CONH₂, alkylaminocarbonyl having 2–7 carbon atoms, dialkylaminocarbonyl having 3–13 carbon atoms in total, amidino, and guanidino; and provided that the heterocyclic group for $R^1$ and $R^5$ is selected from the group consisting of pyridyl, pyrrolidinyl, piperidinyl, furyl, thienyl, piperazinyl, indolyl and benzimidazolyl.

15. A method for treating arthritis which comprises injecting or orally administering into a patient an epoxysuccinamide derivative having the following formula (1) and its physiologically acceptable salt in an amount of 0.01 to 100 mg/day in the case of injection or in an amount of 0.1 mg/day to 1 g/day in the case of oral administration:

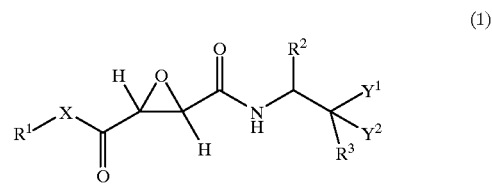

wherein $R^1$ represents a hydrogen atom, an alkyl group having 1 to 10 carbon atoms, an alkenyl group having 2 to 10 carbon atoms, an alkynyl group having 2 to 10 carbon atoms, an aryl group having 6 to 20 carbon atoms, or an aralkyl group consisting of an aryl group having 6 to 20 carbon atoms and an alkyl group having 1 to 6 carbon atoms;

$R^2$ represents an isobutyl group or an isopropyl group;

$R^3$ represents a hydrogen atom or an aryl group having 6 to 20 carbon atoms;

X represents —O— or —NR⁴— in which R⁴ is a hydrogen atom, an alkyl group having 1 to 10 carbon atoms, an aryl group having 6 to 20 carbon atoms, an aralkyl group consisting of an aryl group having 6 to 20 carbon atoms and an alkyl group having 1 to 6 carbon atoms, a heterocyclic group having 3 to 12 carbon atoms, or a heterocyclic-alkyl group consisting of a heterocyclic group having 3 to 12 carbon atoms and an alkyl group having 1 to 6 carbon atoms;

$Y^1$ represents $OR^5$ in which $R^5$ is a hydrogen atom, an alkyl group having 1 to 10 carbon atoms, an aryl group having 6 to 20 carbon atoms, an aralkyl group consisting of an aryl group having 6 to 20 carbon atoms and an alkyl group having 1 to 6 carbon atoms, an acetoxy group, a benzoyloxy group, a heterocyclic group having 3 to 12 carbon atoms, or a heterocyclic-alkyl group consisting of a heterocyclic group having 3 to 12 carbon atoms and an alkyl group having 1 to 6 carbon atoms; and $Y^2$ represents a hydrogen atom;

provided that the alkyl group for $R^5$ may have one or more substituents selected from the group consisting of hydroxyl, amino, alkylamino having 1–6 carbon atoms, dialkylamino having 2–12 carbon atoms in total, alkoxy having 1–6 carbon atoms, carboxyl, alkoxycarbonyl having 2–7 carbon atoms, —CONH₂, alkylaminocarbonyl having 2–7 carbon atoms, dialkylaminocarbonyl having 3–13 carbon atoms in total, and guanidino; provided that the aryl group for $R^1$, $R^3$ and $R^5$ may have one or more substituents selected from the group consisting of alkyl having 1–6 carbon atoms, hydroxyl, amino, alkylamino having 1–6 carbon atoms, dialkylamino having 2–12 carbon atoms in total, alkoxy having 1–6 carbon atoms, halogen, haloalkyl having 1–6 carbon atoms, cyano, nitro, carboxyl, alkoxycarbonyl having 2–7 carbon atoms, —CONH₂, alkylaminocarbonyl having 2–7 carbon atoms, dialkylaminocarbonyl having 3–13 carbon atoms in total, amidino, and guanidino;

provided that the heterocyclic group for $R^5$ may have one or more substituents selected from the group consisting of alkyl having 1–6 carbon atoms, hydroxyl, amino, alkylamino having 1–6 carbon atoms, dialkylamino having 2–12 carbon atoms in total, alkoxy having 1–6 carbon atoms, halogen, haloalkyl having 1–6 carbon atoms, cyano, nitro, carboxyl, alkoxycarbonyl having 2–7 carbon atoms, —$CONH_2$, alkylaminocarbonyl having 2–7 carbon atoms, dialkylaminocarbonyl having 3–13 carbon atoms in total, amidino, and guanidino; and provided that the heterocyclic group for $R^4$ and $R^5$ is selected from the group consisting of pyridyl, pyrrolidinyl, piperidinyl, furyl, thienyl, piperazinyl, indolyl and benzimidazolyl.

* * * * *

… (12) EX PARTE REEXAMINATION CERTIFICATE (6358th)

United States Patent
Nomura et al.

(10) Number: US 6,387,908 C1
(45) Certificate Issued: Aug. 12, 2008

(54) EPOXYSUCCINAMIDE DERIVATIVES

(75) Inventors: Yutaka Nomura, Noda (JP); Toshihiro Takahashi, Misato (JP); Yasushi Yoshino, Funabashi (JP); Koichiro Nishioka, Kasukabe (JP)

(73) Assignee: Nippon Chemiphar Co., Ltd., Chiyoda-Ku, Tokyo (JP)

Reexamination Request:
No. 90/008,090, Jul. 10, 2006

Reexamination Certificate for:
Patent No.: 6,387,908
Issued: May 14, 2002
Appl. No.: 09/508,026
Filed: May 5, 2000

(22) PCT Filed: Sep. 4, 1998

(86) PCT No.: PCT/JP98/03983

§ 371 (c)(1),
(2), (4) Date: May 5, 2000

(87) PCT Pub. No.: WO99/11640

PCT Pub. Date: Mar. 11, 1999

(30) Foreign Application Priority Data

Sep. 4, 1997 (JP) ............................................. 9-257538

(51) Int. Cl.
*C07D 303/00* (2006.01)
*C07D 303/48* (2006.01)
*A61K 31/497* (2006.01)

(52) U.S. Cl. ...................... 514/254.1; 248/467; 248/517; 514/336; 514/394; 514/414; 514/422; 514/444; 514/471; 514/475; 514/326; 544/374; 546/207; 546/281.7; 548/304.7; 548/467; 548/517; 549/472; 549/473; 549/548; 549/549; 549/60

(58) Field of Classification Search .................... None
See application file for complete search history.

(56) References Cited

U.S. PATENT DOCUMENTS

| 5,679,708 A | * | 10/1997 | Tsubotani et al. | ............ 514/475 |
| 5,843,992 A | | 12/1998 | Nomura et al. | .............. 514/475 |
| 6,387,908 B1 | | 5/2002 | Nomura et al. | .......... 514/254.1 |
| 6,689,785 B2 | | 2/2004 | Nomura et al. | .......... 514/254.1 |

FOREIGN PATENT DOCUMENTS

| JP | 63-284127 | 11/1988 |
| JP | 61-55509 | 6/1994 |
| WO | WO 96/30354 | 10/1996 |

* cited by examiner

*Primary Examiner*—Evelyn Mei Huang

(57) ABSTRACT

Epoxysuccinamide derivatives of the formula (1):

wherein $R^1$ is hydrogen, alkyl, alkenyl, alkynyl, aryl, or aralkyl; $R^2$ is alkyl, alkenyl, alkynyl, aryl, or aralkyl; $R^3$ is hydrogen, alkyl, alkenyl, alkynyl, aryl, aralkyl, heterocyclic, or heterocyclic-alkyl; X is —O— or —$NR^4$— ($R^4$ is hydrogen, alkyl, aryl, aralkyl, heterocyclic, or heterocyclic-alkyl); $Y^1$ is $OR^5$, $SR^6$, or $NR^7R^8$; and $Y^2$ is hydrogen or alkyl. The compounds are useful as remedies for bone diseases and arthritis.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 4 is cancelled.

Claims 1, 7 and 12–15 are determined to be patentable as amended.

Claims 2–3, 5–6 and 8–10, dependent on an amended claim, are determined to be patentable.

New claims 16–18 are added and determined to be patentable.

Claim 11 was not reexamined.

1. An epoxysuccinamide derivative having the following formula (1) and its physiologically acceptable salt:

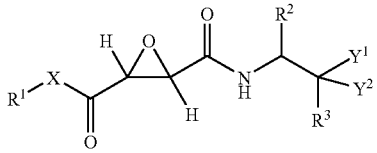

wherein
R$^1$ represents a hydrogen atom, an alkyl group having 1 to 10 carbon atoms, an alkenyl group having 2 to 10 carbon atoms, an alkynyl group having 2 to 10 carbon atoms, an aryl group having 6 to 20 carbon atoms, or an aralkyl group consisting of an aryl group having 6 to 20 carbon atoms and an alkyl group having 1 to 6 carbon atoms;
R$^2$ represents an alkyl group having 1 to 10 carbon atoms, an alkenyl group having 2 to 10 carbon atoms, an alkynyl group having 2 to 10 carbon atoms, an aryl group having 6 to 20 carbon atoms, or an aralkyl group consisting of an aryl group having 6 to 20 carbon atoms and an alkyl group having 1 to 6 carbon atoms;
R$^3$ represents a hydrogen atom[, an alkyl group having 1 to 10 carbon atoms, an alkenyl group having 2 to 10 carbon atoms, an alkynyl group having 2 to 10 carbon atoms, an aryl group having 6 to 20 carbon atoms, an aralkyl group consisting of an aryl group having 6 to 20 carbon atoms and an alkyl group having 1 to 6 carbon atoms, a heterocyclic group having 3 to 12 carbon atoms, or a heterocyclic-alkyl group consisting of a heterocyclic group having 3 to 12 carbon atoms and an alkyl group having 1 to 6 carbon atoms];
X represents —O— or —NR$^4$— in which R$^4$ is a hydrogen atom, an alkyl group having 1 to 10 carbon atoms, an aryl group having 6 to 20 carbon atoms, an aralkyl group consisting of an aryl group having 6 to 20 carbon atoms and an alkyl group having 1 to 6 carbon atoms, a heterocyclic group having 3 to 12 carbon atoms, or a heterocyclic-alkyl group consisting of a heterocyclic group having 3 to 12 carbon atoms and an alkyl group having 1 to 6 carbon atoms;
Y$^1$ represents [a hydroxyl group,] an alkyl group having 1 to 6 carbon atoms, an acetoxy group, or an aralkyloxy group consisting of an aryl group having 6 to 20 carbon atoms and an alkyl group having 1 to 6 carbon atoms; and
Y$^2$ represents a hydrogen atom [-or an alkyl group having 1 to 10 carbon atoms];
provided that the aryl group for R$^1$ to R$^4$ may have one or more substituents selected from the group consisting of alkyl having 1–6 carbon atoms, hydroxyl, amino, alkylamino having 1–6 carbon atoms, dialkylamino having 2–12 carbon atoms in total, alkoxy having 1–6 carbon atoms, halogen, haloalkyl having 1–6 carbon atoms, cyano, nitro, carboxyl, alkoxy-carbonyl having 2–7 carbon atoms, —CONH$_2$, alkylaminocarbonyl having 2–7 carbon atoms, dialkylaminocarbonyl having 3–13 carbon atoms in total, amidino, and guanidino; and
provided that the heterocyclic group for R$^3$ and R$^4$ is selected from the group consisting of pyridyl, pyrrolidinyl, piperidinyl, furyl, thienyl, piperazinyl, indolyl and benzimidazolyl.

7. An epoxysuccinamide derivative having the following formula (1) and its physiologically acceptable salt:

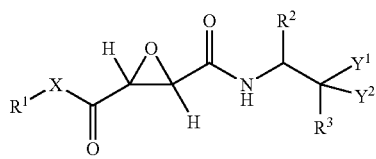

wherein
R$^1$ represents a hydrogen atom, an alkyl group having 1 to 10 carbon atoms, an alkenyl group having 2 to 10 carbon atoms, an alkynyl group having 2 to 10 carbon atoms, an aryl group having 6 to 20 carbon atoms, or an aralkyl group consisting of an aryl group having 6 to 20 carbon atoms and an alkyl group having 1 to 6 carbon atoms;
R$^2$ represents an isobutyl group or an isopropyl group;
R$^3$ represents a hydrogen atom [or an aryl group having 6 to 20 carbon atoms];
X represents —O— or —NR$^4$— in which R$^4$ is a hydrogen atom, an alkyl group having 1 to 10 carbon atoms, an aryl group having 6 to 20 carbon atoms, an aralkyl group consisting of an aryl group having 6 to 20 carbon atoms and an alkyl group having 1 to 6 carbon atoms, a heterocyclic group having 3 to 12 carbon atoms, or a heterocyclic-alkyl group consisting of a heterocyclic group having 3 to 12 carbon atoms and an alkyl group having 1 to 6 carbon atoms;
Y$^1$ represents OR$^5$ in which R$^5$ is [a hydrogen atom,] an alkyl group having 1 to 10 carbon atoms, an aryl group having 6 to 20 carbon atoms, an aralkyl group consisting of an aryl group having 6 to 20 carbon atoms and an alkyl group having 1 to 6 carbon atoms, an acetoxy group, a benzoyloxy group, a heterocyclic group having 3 to 12 carbon atoms, or a heterocyclic-alkyl group consisting of a heterocyclic group having 3 to 12 carbon atoms and an alkyl group having 1 to 6 carbon atoms; and Y² represents a hydrogen atom;
provided that the alkyl group for R⁵ may have one or more substituents selected from the group consisting of hydroxyl, amino, alkylamino having 1–6 carbon atoms, dialkylamino having 2–12 carbon atoms in total, alkoxy having 1–6 carbon atoms, carboxyl, alkoxycarbonyl having 2–7 carbon atoms, —CONH₂, alkylaminocarbonyl having 2–7 carbon atoms, dialkylaminocarbonyl having 3–13 carbon atoms in total, and guanidino; provided that the aryl group for R¹, R³ and R⁵ may have one or more substituents selected from the group consisting of alkyl having 1–6 carbon atoms, hydroxyl, amino, alkylamino having 1–6 carbon atoms, dialkylamino having 2–12 carbon atoms in total, alkoxy having 1–6 carbon atoms, halogen, haloalkyl having 1–6 carbon atoms, cyano, nitro, carboxyl, alkoxycarbonyl having 2–7 carbon atoms, —CONH₂, alkylaminocarbonyl having 2–7 carbon atoms, dialkylaminocarbonyl having 3–13 carbon atoms in total, amidino, and guanidino;
provided that the heterocyclic group for R⁵ may have one or more substituents selected from the group consisting of alkyl having 1–6 carbon atoms, hydroxyl, amino, alkylamino having 1–6 carbon atoms, dialkylamino having 2–12 carbon atoms in total, alkoxy having 1–6 carbon atoms, halogen, haloalkyl having 1–6 carbon atoms, cyano, nitro, carboxyl, alkoxycarbonyl having 2–7 carbon atoms, —CONH₂, alkylaminocarbonyl having 2–7 carbon atoms, dialkylaminocarbonyl having 3-13 carbon atoms in total, amidino, and guanidino; and
provided that the heterocyclic group for R³, R⁴ and R⁵ is selected from the group consisting of pyridyl, pyrrolidinyl, piperidinyl, furyl, thienyl, piperazinyl, indolyl and benzimidazolyl.

12. A method of treating a bone disease selected from the group consisting of osteoporosis, malignant hypercalcemia and Paget's disease, the method comprising injecting or orally administering into a patient an epoxysuccinamide derivative having the following formula (1) and is physiologically acceptable salt in an amount of 0.01 to 100 mg/day in the case of injection or in an amount of 0.1 mg/day to 1 g/day in the case of oral administration:
wherein
R¹ represents a hydrogen atom, an alkyl group having 1 to 10 carbon atoms, an alkenyl group having 2 to 10 carbon atoms, an alkynyl group having 2 to 10 carbon atoms, an aryl group having 6 to 20 carbon atoms, or an aralkyl group consisting of an aryl group having 6 to 20 carbon atoms and an alkyl group having 1 to 6 carbon atoms;
R² represents an alkyl group having 1 to 10 carbon atoms, an alkenyl group having 2 to 10 carbon atoms, an alkynyl group having 2 to 10 carbon atoms, an aryl group having 6 to 20 carbon atoms, or an aralkyl group consisting of an aryl group having 6 to 20 carbon atoms and an alkyl group having 1 to 6 carbon atoms;
R³ represents a hydrogen atom[, an alkyl group having 1 to 10 carbon atoms, an alkenyl group having 2 to 10 carbon atoms, an alkynyl group having 2 to 10 carbon atoms, an aryl group having 6 to 20 carbon atoms, an aralkyl group consisting of an aryl group having 6 to 20 carbon atoms and an alkyl group having 1 to 6 carbon atoms, a heterocyclic group having 3 to 12 carbon atoms, or a heterocyclic-alkyl group consisting of a heterocyclic group having 3 to 12 carbon atoms and an alkyl group having 1 to 6 carbon atoms];

X represents —O— or —NR⁴— in which R⁴ is a hydrogen atom, an alkyl group having 1 to 10 carbon atoms, an aryl group having 6 to 20 carbon atoms, an aralkyl group consisting of an aryl group having 6 to 20 carbon atoms and an alkyl group having 1 to 6 carbon atoms, a heterocyclic group having 3 to 12 carbon atoms, or a heterocyclic-alkyl group consisting of a heterocyclic group having 3 to 12 carbon atoms and an alkyl group having 1 to 6 carbon atoms;
Y¹ represents [a hydroxyl group,] an alkoxy group having 1 to 6 carbon atoms, an acetoxy group, or an aralkyloxy group consisting of an aryl group having 6 to 20 carbon atoms and an alkyl group having 1 to 6 carbon atoms; and
Y² represents a hydrogen atom [or an alkyl group having 1 to 10 carbon atoms];
provided that the aryl group for R¹ to R⁴ may have one or more substituents selected from the group consisting of alkyl having 1–6 carbon atoms, hydroxyl, amino, alkylamino having 1–6 carbon atoms, dialkylamino having 2–12 carbon atoms in total, alkoxy having 1–6 carbon atoms, halogen, haloalkyl having 1–6 carbon atoms, cyano, nitro, carboxyl, alkoxy-carbonyl having 2–7 carbon atoms, —CONH₂, alkylaminocarbonyl having 2–7 carbon atoms, dialkylaminocarbonyl having 3–13 carbon atoms in total, amidino, and guanidino; and
provided that the heterocyclic group for R³ and R⁴ is selected from the group consisting of pyridyl, pyrrolidinyl, piperidinyl, furyl, thienyl, piperazinyl, indolyl and benzimidazolyl.

13. A method for treating arthritis which comprises injecting or orally administering into a patient an epoxy succinamide derivative having the following formula (1) and its physiologically acceptable salt in an amount of 0.01 to 100 mg/day in the case of injection or in an amount of 0.1 mg/day to 1 g/day in the case of oral administration:

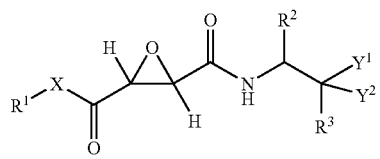

wherein
R¹ represents a hydrogen atom, an alkyl group having 1 to 10 carbon atoms, an alkenyl group having 2 to 10 carbon atoms, an alkynyl group having 2 to 10 carbon atoms, an aryl group having 6 to 20 carbon atoms, or an aralkyl group consisting of an aryl group having 6 to 20 carbon atoms and an alkyl group having 1 to 6 carbon atoms;
R² represents an alkyl group having 1 to 10 carbon atoms, an alkenyl group having 2 to 10 carbon atoms, an alkynyl group having 2 to 10 carbon atoms, an aryl group having 6 to 20 carbon atoms, or an aralkyl group consisting of an aryl group having 6 to 20 carbon atoms and an alkyl group having 1 to 6 carbon atoms;
R³ represents a hydrogen atom[, an alkyl group having 1 to 10 carbon atoms, an alkenyl group having 2 to 10 carbon atoms, an alkynyl group having 2 to 10 carbon atoms, an aryl group having 6 to 20 carbon atoms, an aralkyl group consisting of an aryl group having 6 to 20 carbon atoms and an alkyl group having 1 to 6 carbon atoms, a heterocyclic group having 3 to 12 carbon atoms, or a heterocyclic-alkyl group consisting of a heterocyclic group having 3 to 12 carbon atoms and an alkyl group having 1 to 6 carbon atoms];

X represents —O— or —NR$^4$— in which R$^4$ is a hydrogen atom, an alkyl group having 1 to 10 carbon atoms, an aryl group having 6 to 20 carbon atoms, an aralkyl group consisting of an aryl group having 6 to 20 carbon atoms and an alkyl group having 1 to 6 carbon atoms, a heterocyclic group having 3 to 12 carbon atoms, or a heterocyclic-alkyl group consisting of a heterocyclic group having 3 to 12 carbon atoms and an alkyl group having 1 to 6 carbon atoms;

Y$^1$ represents [a hydroxyl group,] an alkoxy group having 1 to 6 carbon atoms, an acetoxy group, or an aralkyloxy group consisting of an aryl group having 6 to 20 carbon atoms and an alkyl group having 1 to 6 carbon atoms; and Y$^2$ represents a hydrogen atom [or an alkyl group having 1 to 10 carbon atoms];

provided that the aryl group for R$^1$ to R$^4$ may have one or more substituents selected from the group consisting of alkyl having 1–6 carbon atoms, hydroxyl, amino, alkylamino having 1–6 carbon atoms, dialkylamino having 2–12 carbon atoms in total, alkoxy having 1–6 carbon atoms, halogen, haloalkyl having 1–6 carbon atoms, cyano, nitro, carboxyl, alkoxy-carbonyl having 2–7 carbon atoms, —CONH$_2$, alkylaminocarbonyl having 2–7 carbon atoms, dialkylaminocarbonyl having 3–13 carbon atoms in total, amidino, and guanidino; and provided that the heterocyclic group for R$^3$ and R$^4$ is selected from the group consisting of pyridyl, pyrrolidinyl, piperidinyl, furyl, thienyl, piperazinyl, indolyl and benzimidazolyl.

14. A method of treating a bone disease selected from the group consisting of osteoporosis, malignant hypercalcemia and Paget's disease, the method comprising injecting or orally administering into a patient an epoxysuccinamide derivative having the following formula (1) and is physiologically acceptable salt in an amount of 0.01 to 100 mg/day in the case of injection or in an amount of 0.1 mg/day to 1 g/day in the case of oral administration:

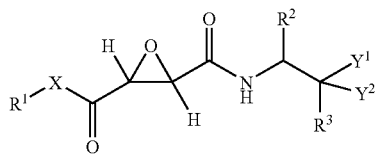

wherein

R$^1$ represents a hydrogen atom, an alkyl group having 1 to 10 carbon atoms, an alkenyl group having 2 to 10 carbon atoms, an alkynyl group having 2 to 10 carbon atoms, an aryl group having 6 to 20 carbon atoms, or an aralkyl group consisting of an aryl group having 6 to 20 carbon atoms and an alkyl group having 1 to 6 carbon atoms;

R$^2$ represents an isobutyl group or an isopropyl group;

R$^3$ represents a hydrogen atom [or an aryl group having 6 to 20 carbon atoms];

X represents —O— or —NR$^4$— in which R$^4$ is a hydrogen atom, an alkyl group having 1 to 10 carbon atoms, an aryl group having 6 to 20 carbon atoms, an aralkyl group consisting of an aryl group having 6 to 20 carbon atoms and an alkyl group having 1 to 6 carbon atoms, a heterocyclic group having 3 to 12 carbon atoms, or a heterocyclic-alkyl group consisting of a heterocyclic group having 3 to 12 carbon atoms and an alkyl group having 1 to 6 carbon atoms;

Y$^1$ represents OR$^5$ in which R$^5$ is [a hydrogen atom,] an alkyl group having 1 to 10 carbon atoms, an aryl group having 6 to 20 carbon atoms, an aralkyl group consisting of an aryl group having 6 to 20 carbon atoms and an alkyl group having 1 to 6 carbon atoms, an acetoxy group, a benzoyloxy group, a heterocyclic group having 3 to 12 carbon atoms, or a heterocyclic-alkyl group consisting of a heterocyclic group having 3 to 12 carbon atoms and an alkyl group having 1 to 6 carbon atoms; and Y$^2$ represents a hydrogen atom;

provided that the alkyl group for R$^5$ may have one or more substituents selected from the group consisting of hydroxyl, amino, alkylamino having 1–6 carbon atoms, dialkylamino having 2–12 carbon atoms in total, alkoxy having 1–6 carbon atoms, carboxyl, alkoxy-carbonyl having 2–7 carbon atoms, —CONH$_2$, alkylaminocarbonyl having 2–7 carbon atoms, dialkylaminocarbonyl having 3–13 carbon atoms in total, and guanidino; provided that the aryl group for R$^1$, R$^3$ and R$^5$ may have one or more substituents selected from the group consisting of alkyl having 1–6 carbon atoms, hydroxyl, amino, alkylamino having 1–6 carbon atoms, dialkylamino having 2–12 carbon atoms in total, alkoxy having 1–6 carbon atoms, halogen, haloalykl having 1–6 carbon atoms, cyano, nitro, carboxyl, alkoxycarbonyl having 2–7 carbon atoms, —CONH$_2$, alkylaminocarbonyl having 2–7 carbon atoms, dialkylaminocarbonyl having 3–13 carbon atoms in total, amidino, and guanidino;

provided that the heterocyclic group for R$^5$ may have one or more substituents selected from the group consisting of alkyl having 1–6 carbon atoms, hydroxyl, amino, alkylamino having 1–6 carbon atoms, dialkylamino having 2–12 carbon atoms in total, alkoxy having 1–6 carbon atoms, halogen, haloalkyl having 1–6 carbon atoms, cyano, nitro, carboxyl, alkoxycarbonyl having 2–7 carbon atoms, —CONH$_2$, alkylaminocarbonyl having 2–7 carbon atoms, dialkylaminocarbonyl having 3–13 carbon atoms in total, amidino, and guanidino; and provided that the heterocyclic group for R$^3$, R$^4$ and R$^5$ is selected from the group consisting of pyridyl, pyrrolidinyl, piperidinyl, furyl, thienyl, piperazinyl, indolyl and benzimidazolyl.

15. A method of treating arthritis which comprises injecting or orally administering into a patient an epoxy succinamide derivative having the following formula (1) and its physiologically acceptable salt in an amount of 0.01 to 100 mg/day in the case of injection or in an amount of 0.1 mg/day to 1 g/day in the case of oral administration:

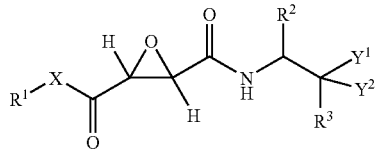

wherein

R$^1$ represents a hydrogen atom, an alkyl group having 1 to 10 carbon atoms, an alkenyl group having 2 to 10 carbon atoms, an alkynyl group having 2 to 10 carbon atoms, an aryl group having 6 to 20 carbon atoms, or an aralkyl group consisting of an aryl group having 6 to 20 carbon atoms and an alkyl group having 1 to 6 carbon atoms;

R$^2$ represents an isobutyl group or an isopropyl group;

R$^3$ represents a hydrogen atom [or an aryl group having 6 to 20 carbon atoms];

X represents —O— or —NR$^4$— in which R$^4$ is a hydrogen atom, an alkyl group having 1 to 10 carbon atoms, an aryl group having 6 to 20 carbon atoms, an aralkyl group consisting of an aryl group having 6 to 20 carbon atoms and an alkyl group having 1 to 6 carbon atoms, a heterocyclic group having 3 to 12 carbon atoms, or a heterocyclic-alkyl group consisting of a heterocyclic group having 3 to 12 carbon atoms and an alkyl group having 1 to 6 carbon atoms;

Y$^1$ represents OR$^5$ in which R$^5$ is [a hydrogen atom,] an alkyl group having 1 to 10 carbon atoms, an aryl group having 6 to 20 carbon atoms, an aralkyl group consisting of an aryl group having 6 to 20 carbon atoms and an alkyl group having 1 to 6 carbon atoms, an acetoxy group, a benzoyloxy group, a heterocyclic group having 3 to 12 carbon atoms, or a heterocyclic-alkyl group consisting of a heterocyclic group having 3 to 12 carbon atoms and an alkyl group having 1 to 6 carbon atoms; and Y$^2$ represents a hydrogen atom;

provided that the alkyl group for R$^5$ may have one or more substituents selected from the group consisting of hydroxyl, amino, alkylamino having 1–6 carbon atoms, dialkylamino having 2–12 carbon atoms in total, alkoxy having 1–6 carbon atoms, carboxyl, alkoxycarbonyl having 2–7 carbon atoms, —CONH$_2$, alkylaminocarbonyl having 2–7 carbon atoms, dialkylaminocarbonyl having 3–13 carbon atoms in total, and guanidino; provided that the aryl group for R$^1$, R$^3$ and R$^5$ may have one or more substituents selected from the group consisting of alkyl having 1–6 carbon atoms, hydroxyl, amino, alkylamino having 1–6 carbon atoms, dialkylamino having 2–12 carbon atoms in total, alkoxy having 1–6 carbon atoms, halogen, haloalkyl having 1–6 carbon atoms, cyano, nitro, carboxyl, alkoxycarbonyl having 2–7 carbon atoms, —CONH$_2$, alkylaminocarbonyl having 2–7 carbon atoms, dialkylaminocarbonyl having 3–13 carbon atoms in total; amidino, and guanidino;

provided that the heterocyclic group for R$^5$ may have one or more substituents selected from the group consisting of alkyl having 1–6 carbon atoms, hydroxyl, amino, alkylamino having 1–6 carbon atoms, dialkylamino having 2–12 carbon atoms in total, alkoxy having 1–6 carbon atoms, halogen, haloalkyl having 1–6 carbon atoms, cyano, nitro, carboxyl, alkoxycarbonyl having 2–7 carbon atoms, —CONH$_2$, alkylaminocarbonyl having 2–7 carbon atoms, dialkylaminocarbonyl having 3–13 carbon atoms in total, amidino, and guanidino; and provided that the heterocyclic group for R$^3$, R$^4$ and R$^5$ is selected from the group consisting of pyridyl, pyrrolidinyl, piperidinyl, furyl, thienyl, piperazinyl, indolyl and benzimidazolyl.

16. The epoxysuccinamide derivative of the formula (1) and its physiologically acceptable salt defined in claim 1, which is selected from the group consisting of:

ethyl (2S,3S)-3-[[1-(S)-benzyloxymethyl-2-phenylethyl]-carbamoyl]oxirane-2-carboxylate;

ethyl (2S,3S)-3-[[1-(S)-isobutoxymethyl-2-phenylethyl]-carbamoyl]oxirane-2-carboxylate;

sodium (2S,3S)-3-[[1-(S)-benzyloxymethyl-2-phenylethyl]-carbamoyl]oxirane-2-carboxylate; and ethyl (2S,3S)-3-[[1-(S)-isobutoxymethyl-2-methylbutyl]-carbamoyl]oxirane-2-carboxylate.

17. The epoxysuccinamide derivative of the formula (1) and its physiologically acceptable salt defined in claim 7, which is selected from the group consisting of:

ethyl (2S,3S)-3-[[1-(S)-(3-pyridyl)methoxymethyl-3-methylbutyl]carbamoyl]oxirane-2-carboxylate;

ethyl (2S,3S)-3-[[1-(S)-(3-thienyl)methoxymethyl-3-methylbutyl]carbamoyl]oxirane-2-carboxylate;

ethyl (2S,3S)-3-[[1-(S)-(2-benzimidazolyl)methoxymethyl-3-methylbutyl]carbamoyl]oxirane-2-carboxylate;

ethyl (2S,3S)-3-[[1-(S)-phenoxymethyl-3-methylbutyl]carbamoyl]oxirane-2-carboxylate;

ethyl (2S,3S)-3-[[1-(S)-(2-methoxyethoxy)methyl-3-methylbutyl]carbamoyl]oxirane-2-carboxylate;

ethyl (2S,3S)-3-[[1-(S)-[(dimethylcarbamoyl)methoxy]methyl-3-methylbutyl]carbamoyl]oxirane-2-carboxylate;

ethyl (2S,3S)-3-[[1-(S)-(4-diethylaminobutyloxy)methyl-3-methylbutyl]carbamoyl]oxirane-2-carboxylate;

ethyl (2S,3S)-3-[[1-(S)-(4-isopropylbenzyloxy)methyl-3-methylbutyl]carbamoyl]oxirane-2-carboxylate;

ethyl (2S,3S)-3-[[1-(S)-(2-chlorobenzyloxy)methyl-3-methylbutyl]carbamoyl]oxirane-2-carboxylate;

ethyl (2S,3S)-3-[[1-(S)-(3-aminobenzyloxy)methyl-3-methylbutyl]carbamoyl]oxirane-2-carboxylate;

ethyl (2S,3S)-3-[[1-(S)-benzyloxymethyl-3-methylbutyl]carbamoyl]oxirane-2-carboxylate;

ethyl (2S,3S)-3-[[1-(S)-isobutoxymethyl-3-methylbutyl]carbamoyl]oxirane-2-carboxylate;

ethyl (2S,3S)-3-[[1-(R)-isobutoxymethyl-3-methylbutyl]carbamoyl]oxirane-2-carboxylate;

sodium (2S,3S)-3-[[1-(S)-benzyloxymethyl-3-methylbutyl]carbamoyl]oxirane-2-carboxylate;

ethyl (2S,3S)-3-[[1-(S)-(2-phenylethoxy)methyl-3-methylbutyl]carbamoyl]oxirane-2-carboxylate;

ethyl (2S,3S)-3-[[1-(S)-(3-methylbutyloxy)methyl-3-methylbutyl]carbamoyl]oxirane-2-carboxylate;

ethyl (2S,3S)-3-[[1-(S)-hexyloxymethyl-3-methylbutyl]carbamoyl]oxirane-2-carboxylate;

isopropyl (2S,3S)-3-[[1-(S)-isobutoxymethyl-3-methylbutyl]carbamoyl]oxirane-2-carboxylate;

tert-butyl (2S,3S)-3-[[1-(S)-isobutoxymethyl-3-methylbutyl]carbamoyl]oxirane-2-carboxylate;

phenyl (2S,3S)-3-[[1-(S)-isobutoxymethyl-3-methylbutyl]carbamoyl]oxirane-2-carboxylate;

4-tert-butylphenyl (2S,3S)-3-[[1-(S)-isobutoxymethyl-3-methylbutyl]carbamoyl]oxirane-2-carboxylate;

sodium (2S,3S)-3-[[1-(S)-isobutoxymethyl-3-methylbutyl]carbamoyl]oxirane-2-carboxylate;

ethyl (2S,3S)-3-[[1-(S)-isobutoxymethyl-2-methylpropyl]carbamoyl]oxirane-2-carboxylate;

ethyl (2S,3S)-3-[[1-(S)-diphenylmethoxymethyl-3-methylbutyl]carbamoyl]oxirane-2-carboxylate;

cyclohexyl (2S,3S)-3-[[1-(S)-isobutoxymethyl-3-methylbutyl]carbamoyl]oxirane-2-carboxylate;

ethyl (2S,3S)-3-[[1-(S)-(cyclopropylmethoxy)methyl-3-methylbutyl]carbamoyl]oxirane-2-carboxylate; and ethyl (2S,3S)-3-[[1-(S)-(cyclohexylmethoxy)methyl-3-methylbutyl]carbamoyl]oxirane-2-carboxylate.

18. An epoxysuccinamide selected from the group consisting of:

ethyl (2S,3S)-3-[[1-(S)-[α-(R)-hydroxybenzyl]-3-methylbutyl]carbamoyl]oxirane-2-carboxylate;

(2S,3S)-3-[[(αS, βR)-β-hydroxy-α-phenyl]phenethyl]carbamoyloxirane-2-carboxylic acid;

(2S,3S)-3-[[1-(S)-[α-(R)-methoxybenzyl]-3-methylbutyl]carbamoyl]oxirane-2-carboxylic acid;

(2S,3S)-3-[[1(S)-hydroxymethyl-3-methylbutyl]carbamoyl]oxirane-2-carboxylic acid;

ethyl (2S,3S)-3-[[1-(S)-[α-(R)-acetoxybenzyl]-3-methylbutyl]carbamoyl]oxirane-2-carboxylate;

isopropyl (2S,3S)-3-[[1-(S)-[α-(R)-methoxybenzyl]-3-methylbutyl]carbamoyl]oxirane-2-carboxylate;

benzyl (2S,3S)-3-[[1-(S)-[α-(R)-methoxybenzyl]-3-methylbutyl]carbamoyl]oxirane-2-carboxylate;

ethyl (2S,3S)-3-[[1-(S)-[α-(R)-benzyloxybenzyl]-3-methylbutyl]carbamoyl]oxirane-2-carboxylate;

ethyl (2R,3R)-3-[[1-(S)-[α-(R)-hydroxybenzyl]-3-methylbutyl]carbamoyl]oxirane-2-carboxylate;

(2S,3S)-3-[[1-(S)-[α-(R)-hydroxybenzyl]-3-methylbutyl]carbamoyl]oxirane-2-carboxylic acid;

(2S,3S)-3-[[1-(S)-[α-(R)-(benzyloxy)benzyl]-3-methylbutyl]carbamoyl]oxirane-2-carboxylic acid;

ethyl (2S,3S)-3-[[1-(S)-[α-(R)-hydroxybenzyl]-2-methylbutyl]carbamoyl]oxirane-2-carboxylate;

ethyl (2S,3S)-3-[[(αS,βR)-β-hydroxy-α-phenyl]phenethyl]carbamoyloxirane-2-carboxylate;

ethyl (2S,3S)-3-[[1-(S)-[α-(R)-methoxybenzyl]-3-methylbutyl]carbamoyl]oxirane-2-carboxylate;

ethyl (2S,3S)-3-[[1-(S)-hydroxymethyl-3-methylbutyl]carbamoyl]oxirane-2-carboxylate;

(2S,3S)-3-[[1-(S)-[α-(R)-hydroxybenzyl]-2-methylbutyl]carbamoyl]oxirane-2-carboxylate; and ethyl (2S,3S)-3-[[1-(S)-[(R)-cyclohexyl(methoxy)methyl]-3-methylbutyl]carbamoyl]oxirane-2-carboxylate.

\* \* \* \* \*